United States Patent
Simon et al.

(10) Patent No.: US 10,159,212 B1
(45) Date of Patent: Dec. 25, 2018

(54) DOWNY MILDEW RESISTANT/TOLERANT SWEET BASIL VARIETIES

(71) Applicant: Rutgers, The State University of New Jersey, New Brunswick, NJ (US)

(72) Inventors: James E. Simon, Princeton, NJ (US); Robert Michael Pyne, Palm Desert, CA (US); Christain Andrew Wyenandt, Elmer, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/812,968

(22) Filed: Nov. 14, 2017

(51) Int. Cl.
*A01H 5/12* (2018.01)
*A01H 6/50* (2018.01)

(52) U.S. Cl.
CPC .............. *A01H 6/506* (2018.05); *A01H 5/12* (2013.01)

(58) Field of Classification Search
None
See application file for complete search history.

(56) References Cited

U.S. PATENT DOCUMENTS

2018/0265887 A1 9/2018 Acosta et al.

OTHER PUBLICATIONS

Grayer et al 1996, Phytochemistry 43(5): 1033-1039.*
Hao et al 1996, Phytochemistry 43(4): 735-739.*
Homa et al., "Evaluation of Fungicides for the Control of *Peronospora belbahrii* on Sweet Basil in New Jersey," *Plant Dis.* 98:1561-1566, 2014.
Homa et al., "Morphological Characteristics and Susceptibility of *Basil* Species and Cultivars to *Peronospora belbahrii*," *HortScience* 51:1389-1396, 2016.
Koroch et al., "Rapid staining method to detect and identify downy mildew (*Peronospora belbahrii*) in basil," *Applications in Plant Sciences* 1:1300032, 2013.
McGrath, M.T., Cornell University: Vegetable MD Online, "Expect and Prepare for Downy Mildew in Basil," vegetablemdonline.path.cornell.edu/NewsArticles/BasilDowny.html, 2011.
Pyne et al., "A first linkage map and downy mildew resistance QTL discovery for sweet basil (*Ocimum basilicum*) facilitated by double digestion restriction site associated DNA sequencing (ddRADseq)," *PLoS One* 12:e0184319, 2017.
Pyne et al., "A Rapid Screening Approch to Identify Resistance to Basil Downy Mildew (*Peronospora belbahrii*)," *HortScience* 49:1041-1045, 2014.
Pyne et al., "Inheritance of Resistance to Downy Mildew in Sweet Basil," *J Amer Soc Hort Sci.* 140:396-403, 2015.
Pyne, "A first linkage map and downy mildew resistance QTL discovery for sweet basil (*Ocimum basilicum*) facilitated by double digestion restriction site associated DNA sequencing (ddRADseq)," PLoS One, Manuscript Draft, 2017, 62 pages.
Simon et al., "Basil: A source of essential oils," pp. 484-489 in *Advances in New Crops*, J. Janick and J.E. Simon (eds.), Timber Press, Portland, OR, 1990.
Simon et al., "Basil: A source of aroma compounds and a popular culinary and ornamental herb," pp. 499-505 in *Perspectives on New Crops and New Uses*, J. Janick (ed.), ASHS Press, Alexandria, VA, 1999.
Villani et al., "An improved clearing and mounting solution to replace choral hydrate in microscopic application," *Applications in Plant Sciences* 1:1300016, 2013.
Wyenandt et al., "Basil Downy Mildew (*Peronospora belbahrii*): Discoveries and Challenges Relative to Its Control," *Phytopathol.* 105:885-894, 2015.
Wyenandt et al., "Susceptibility of Basil Cultivars and Breeding Lines to Downy Mildew (*Peronospora belbahrii*)," *HortTech* 45:1416-1419, 2010.
*Ocimum basilicum* L. 'Prospera', Application No. 2017/2792, Community Plant Variety Office Gazette, p. 61, Feb. 15, 2018.
Pyne et al., "Population structure, genetic diversity and downy mildew resistance among *Ocimum* species germplasm," *BMC Plant Biol.* 18:69, 2018.
Ben-Naim et al., "Transfer of Downy Mildew Resistance from Wild Basil (*Ocimum americanum*) to Sweet Basil (*O. basilicum*)," *Phytopathology* 108:114-123, 2018.

\* cited by examiner

*Primary Examiner* — David H Kruse
(74) *Attorney, Agent, or Firm* — Klarquist Sparkman, LLP

(57) ABSTRACT

Eight new sweet basil (*Ocimum basilicum* L.) cultivars designated 'Rutgers Thunderstruck-DMR', 'Rutgers Passion-DMR', Rutgers Obsession-DMR', 'Rutgers Devotion-DMR', '26_24_33', '50_03_05', '50_03_34', and '42_21_02' are provided, as are parts of the plants, extracts and biomasses from the variety, and uses thereof, for example as a food or in a food product. These plants have basil downy mildew resistance/tolerance.

30 Claims, 7 Drawing Sheets
(6 of 7 Drawing Sheet(s) Filed in Color)
Specification includes a Sequence Listing.

DOWNY MILDEW RESISTANT/TOLERANT SWEET BASIL VARIETIES

ACKNOWLEDGMENT OF GOVERNMENT SUPPORT

This invention was made with government support under 2011-51181-30646 and 2016-68004-24931 awarded by The United States United Department of Agriculture (USDA), and under US-4947-16R awarded by the Binational Agricultural Research & Development (BARD). The government has certain rights in the invention.

FIELD

The present disclosure provides new sweet basil (*Ocimum basilicum* L.) cultivars designated 'Thunderstruck', 'Passion', 'Obsession', 'Rutgers Devotion DMR', '26_24_33', '50_03_05', '50_03_34', and '42_21_02', as well as the parents thereof ('SB22' and 'Mrihani') parts of the plants, extracts and biomasses from these varieties, and uses thereof, for example as a food or in a food product or for ornamental applications, as well as breeding material.

BACKGROUND

Sweet basil (*Ocimum basilicum* L.) is one of the most popular and economically important culinary herbs in North America and Europe. This plant species is used in fresh, dried, essential oil and ornamental horticultural industries. The greater *Ocimum* genus is characterized by a great variability in its genetics, genomic structure, morphology, and essential oil composition (Marotti et al., J Agric Food Chem. 44:3926-9, 1996; Simon et al., Basil: A source of aroma compounds and a popular culinary and ornamental herb. Pages 499-505 in: Perspectives on New Crops and New Uses. J. Janick, ed. ASHS Press, Alexandria, Va., 1999; Vieira et al., J. Am. Soc. Hortic. Sci. 128: 94-99, 2003; Vieira et al., Flavour Fragr J. 21:214-221, 2006; Koroch et al., Israel J. Plant Science 58:183-189, 2010). Their unique capacity to manufacture a wide array of volatile constituents through the phenylpropanoid and terpenoid pathways has generated extensive interest and research in basil's aromatic volatile synthesis and plant secondary metabolism. Each *Ocimum* spp. produces essential oils with varying compositions and levels of volatile constituents distinct to each genotype (chemotype) and conferring unique flavor/aroma profiles (Charles and Simon, J. Essential Oil Research 4:231-23, 1992; Simon et al., Basil: A source of essential oils. *Advances in New Crops*, Timber Press, Portland, Oreg. pp. 484-489, 1990; Simon et al., Basil: A source of aroma compounds and a popular culinary and ornamental herb. Pages 499-505 in: Perspectives on New Crops and New Uses. J. Janick, ed. ASHS Press, Alexandria, Va. 1999; Vieira and Simon, J. Economic Botany: 54(2):207-216, 2000; Vieira et al., Biochemical Systematics and Ecology, 29/3:287-3, 2001). Although the wide diversity in chemotypes is exploited in various specialty industries such as in essential oils, the major United States and European markets demand a specific flavor dominated by monoterpene linalool and complemented by lower concentrations of phenylpropenes such as methyl chavicol and other terpenes including 1,8 cineole (Marotti et al., J Agric Food Chem. 44: 3926-9, 1996; Simon et al., Basil: A source of aroma compounds and a popular culinary and ornamental herb. Pages 499-505 in: Perspectives on New Crops and New Uses. J. Janick, ed. ASHS Press, Alexandria, Va., 1999). In addition to the aroma/flavor, the physical appearance of the plant (phenotype) varies according to its utility in the 1) fresh; 2) processed consumer market; or 3) ornamental/home horticultural and potted plant markets. Within the processed market basil is primarily consumed as a 2A) frozen or 2B) dried or freeze dried product. It is generally observed that market 1B prefers a concave leaf shape, while markets 1A, 2A and 2B prefer a less concave 'large leaf' type. The large leaf type basil varieties are associated with high yield (i.e., foliar volume) with a leaf-to-stem ratio suited for this whereas the concave leaf type varieties tailored to market 1B are often less vigorous and have lower leaf-to-stem ratios, but are more aesthetically pleasing to the consumer. Recent breeding efforts have seen a proliferation of new basil varieties bred to meet the demands of these markets, both of which continue to grow.

Current sweet basil production is being threatened by basil downy mildew (BDM), the causal pathogen of which is *Peronospora belbahrii* (Belbahri et al., Mycol. Res. 109:1276-1287, 2005; Thines et al., Mycol. Res. 113:532-540, 2009). BDM has caused significant economic damage to the annual sweet basil market in the US, Europe, and in other regions worldwide (Hansford, Rev. Appl. Mycol. 12: 421-422, 1933, Garibaldi et al., Plant Dis. 84:1154, 2004, Garibaldi et al., Plant Dis. 89:683, 2005, McLeod et al., Plant Dis. 90:1115, 2006, Khateri et al., J. Plant Pathol. 89:S70, 2007, Ronco et al., New Disease Reports 18:14, 2008, Safrankova and Hollova, Plant Dis. 98:1579, 2014) with annual losses to reduced acreage and failed crops estimated in the millions of dollars (Wyenandt et al., HortScience 45(9): 1416-1419, 2015). BDM was first identified in Uganda in 1933 (Hansford, Rev. Appl. Mycol. 12: 421-422, 1933), but was not observed in the USA until 2007 when its occurrence was reported in southern Florida. Since then the disease has been reported around the world, and was found to be spread naturally in air currents and via infested seed or transplants (e.g., seedlings) infested with the pathogen and disseminated throughout the EU and North America (Wyenandt et al., HortScience 45(9): 1416-1419, 2015). When environmental conditions are conducive to high disease pressure complete crop losses in both greenhouse and field operations have been reported (Roberts et al., Plant Dis. 93(2):199, 2009; Wick and Brazee, Plant Dis. 93(3):318, 2009; Cohen et al., 97(5):692, 2013; McGrath, Cornell University: Vegetable MD Online; expect and prepare for downy mildew in basil. vegetablemdonline. ppath.cornell.edu/NewsArticles/BasilDowny.html, 2011; McGrath et al., Downy mildew wars: A monitoring program can help growers determine if the basil downy mildew pathogen is present in their area. American Vegetable Grower. February 2010 (4 pages); Wyenandt et al., Phytopathology 105:885-894, 2010). BDM development is rapid during periods of high humidity, mild temperatures, and extended periods of leaf wetness (Spencer D. M. (ed.) 1981. The Downy Mildews. Academic Press, New York; Garibaldi et al., Plant Dis. 89:68, 2005; Garibaldi et al., J. Plant Dis. Prot. 114:6-8, 2007). The asexual spores (sporangia) can be spread via wind current, water dispersal, infection/infestation of transplants and contaminated seed (Farahani-Kofoet et al., Mycol. Prog. 11:961-966, 2012). The unusual versatility by which this obligate parasite can be disseminated is a major reason for its global spread in recent years (Garibaldi et al., J. Plant Dis. Prot. 111:465-469, 2004; Belbahri et al., Mycol. Res. 109:1276-1287, 2005; Thines et al., Mycol. Res. 113:532-540, 2009).

SUMMARY

The present disclosure provides a series of new basil cultivars that are downy mildew resistant (DMR) and/or highly tolerant to basil downy mildew. These cultivars were derived from a single source of resistance followed by a series of crosses between an *Ocimum basilicum* with a non-sweet basil phenotype ('Mrihani') and with 'SB22', which is a Rutgers developed and bred sweet basil phenotype (large-leaf Italian phenotype) having Fusarium Wilt Tolerance (FOB). The resulting crossing and backcrossing over multiple generations, and evaluations under varied controlled greenhouse and field-environments subjected to high inoculum densities of downy mildew inoculum pressure lead to the discovery, identification, and development of eight new cultivars, 'Thunderstruck', 'Passion', 'Obsession', 'Rutgers Devotion DMR', '26_24_33', '50_03_05', '50_03_34', and '42_21_02', which range from BDM resistant to highly tolerant of BDM. These new cultivars are sweet basil phenotypes, having the visual appearance and aroma of traditional sweet basils. Genetic fingerprinting of the eight new cultivars shows that they are each uniquely distinct from any currently available sweet basil. These new cultivars can be used for the fresh, processed, fresh frozen, ornamental and heath markets for growers, processors and horticulturalists/home gardeners.

The eight new sweet basil cultivars were isolated by selection and breeding studies to improve plant growth and production, biomass production, and to ensure that the eight new sweet basils cultivars were phenotypically acceptable as sweet basils. The disclosed family of eight new sweet basil cultivars is inbred to produce uniform seeded progeny.

The present disclosure provides eight new sweet basils 'Thunderstruck', 'Passion', 'Obsession', 'Rutgers Devotion DMR', '26_24_33', '50_03_05', '50_03_34', and '42_21_02' that are resistant or tolerant to BDM, which are uniform and stable and genetically distinct from all basils in the marketplace. Also provided herein are methods of producing these new cultivars, a list of the new cultivars along with descriptors, and examples using somaclonal variations in plant tissue culture and protoplast culture conditions as well as induced mutagenesis technologies that can be used to multiply these new cultivars and inbred lines. The disclosure also provides extracts and aroma profiles of these cultivars, methods of making such extracts and procuring such aromas.

Each of the eight new cultivars (Table 1), as well as the parents thereof, a ('SB22' and 'Mrihani') were deposited with the American Type Culture Collection (ATCC), 10801 University Blvd., Manassas, Va., 20110 on Nov. 14, 2017. The deposit is intended to meet all of the requirements of 37 C.F.R. §§ 1.801-1.809. Access to the deposit will be available during the pendency of the application to the Commissioner of Patents and Trademarks and persons determined by the Commissioner to be entitled thereto upon request. The deposit will be maintained in the depository for a period of 30 years, or 5 years after the last request, or for the effective life of the patent, whichever is longer, and will be replaced if necessary during that period. Applicants do not waive any infringement of rights granted under this patent or under the Plant Variety Protection Act (7 U.S.C. 2321 et seq.).

TABLE 1

Eight new sweet basil varieties and their parents

| Variety name | ATCC Accession No. |
| --- | --- |
| 'Thunderstruck' | PTA-124576 |
| 'Passion' | PTA-124574 |
| 'Obsession' | PTA-124572 |
| 'Rutgers Devotion DMR' | PTA-124578 |
| '26_24_33' | PTA-124575 |
| '50_03_05' | PTA-124573 |
| '50_03_34' | PTA-124571 |
| '42_21_02' | PTA-124577 |
| 'SB22' | PTA-124617 |
| 'Mrihani' | PTA-124616 |

Provided herein are eight new sweet basil cultivars ('Thunderstruck', 'Passion', 'Obsession', 'Rutgers Devotion DMR', '26_24_33', '50_03_05', '50_03_34', and '42_21_02') that are highly resistant to or highly tolerant to BDM, as well as progeny of such plants, plant parts, including leaves, cells, plant protoplasts, plant cells of a tissue culture from which sweet basil plants can be regenerated, plant calli, plant clumps, and plant cells that are intact in plants or parts of plants, such as pollen, ovules flowers, seeds, leaves, stems, roots and the like. Also provided is plurality of one or more of 'Thunderstruck', 'Passion', 'Obsession', 'Rutgers Devotion DMR', '26_24_33', '50_03_05', '50_03_34', and '42_21_02' sweet basil plants grown in a field, or greenhouse or in specialized growth facilities, for example under controlled environmental conditions. In addition to the 'Thunderstruck', 'Passion', 'Obsession', 'Rutgers Devotion DMR', '26_24_33', '50_03_05', '50_03_34', and '42_21_02' sweet basil plant varieties, derivatives of such plants retaining BDM resistance or tolerance are provided. In one example, the disclosure provides sweet basil plants having the genotype of one of the new varieties disclosed herein, for example generated through sexual reproduction. For example, the disclosure provides plants produced by growing the seed of 'Thunderstruck', 'Passion', 'Obsession', 'Rutgers Devotion DMR', '26_24_33', '50_03_05', '50_03_34', and '42_21_02' disclosed herein.

The disclosure includes a tissue culture of regenerable cells of cultivar 'Thunderstruck', 'Passion', 'Obsession', 'Rutgers Devotion DMR', '26_24_33', '50_03_05', '50_03_34', and '42_21_02', as well as plants regenerated therefrom. Such regenerated plants can include, consist essentially of, or consist of the physiological and morphological characteristics of a plant grown from the seed of cultivar 'Thunderstruck', 'Passion', 'Obsession', 'Rutgers Devotion DMR', '26_24_33', '50_03_05', '50_03_34', and '42_21_02'. Exemplary regenerable cells include but are not limited to those from protoplasts or cells, such as those from leaf, stem, protoplast, pollen, ovule, embryo, cotyledon, hypocotyl, meristematic cell, root, root tip, pistil, anther, flower, petal, seed, shoot, stein, or petiole of cultivar 'Thunderstruck', 'Passion', 'Obsession', 'Rutgers Devotion DMR', '26_24_33', '50_03_05', '50_03_34', and '42_21_02' provided herein.

The disclosure provides the detailed description for eight new basils that arose from a series of crosses that led to varieties having, consisting essentially of, or consisting of, the morphological and physiological characteristics of the new varieties provided herein ('Thunderstruck', 'Passion', 'Obsession', 'Rutgers Devotion DMR', '26_24_33', '50_03_05', '50_03_34', and '42_21_02'), such as the characteristics noted in Tables 3 to 9, for example elevated downy mildew resistance/tolerance as compared to other sweet basil varieties. In some examples, the cultivars 'Thunderstruck', 'Passion', 'Obsession', 'Rutgers Devotion DMR', '26_24_33', '50_03_05', '50_03_34', and '42_21_02' provided herein have elevated resistance/tolerance to BDM (Table 6), as compared to other sweet basil varieties. In other embodiments, a sweet basil plant or part thereof (such as an essential oil) provided herein includes a chemical profile as set forth herein, for example as provided in Table 9. For example, the essential oil composition of such a plant may include a chemical profile comprising about a combination of linalool, methyl chavicol 1,8-cineole and of other minor EO constituents above 5% list (each as a relative % of the total essential oil) and recognizing the relative % or absolute naturally will vary be time of harvest, growing area, and with each a characteristic sweet basil aroma (Lee et al., Perfumer & Flavorist 42:37-40,42-50, 2017).

Also provided are genetically modified versions of 'Thunderstruck', 'Passion', 'Obsession', 'Rutgers Devotion DMR', '26_24_33', '50_03_05', '50_03_34', and '42_21_02', such as those that include one or more transgenes that confer a desirable trait, such as one or more of those provided herein. In one example, the 'Thunderstruck', 'Passion', 'Obsession', 'Rutgers Devotion DMR', '26_24_33', '50_03_05', '50_03_34', or '42_21_02', variety is modified using gene editing (such as gene silencing).

Compositions that include a seed (such as a seed of 'Thunderstruck', 'Passion', 'Obsession', 'Rutgers Devotion DMR', '26_24_33', '50_03_05', '50_03_34', and/or '42_21_02') that produces a plant of the disclosure in plant seed growth media are provided. Examples of plant seed growth media include soil and synthetic cultivation medium (e.g., those that include polymers and/or hydrogels), and others known in the art (e.g., see U.S. Pat. No. 4,241,537). The growth media can be in a container or can, for example, be soil in a field or greenhouse. Plant seed growth media can provide adequate physical support for seeds and can retain moisture and/or nutritional components. Examples of characteristics for soils can be found, for instance, in U.S. Pat. Nos. 3,932,166 and 4,707,176.

Also provided is a tissue culture of regenerable cells of a disclosed sweet basil plant ('Thunderstruck', 'Passion', 'Obsession', 'Rutgers Devotion DMR', '26_24_33', '50_03_05', '50_03_34', and '42_21_02'), such as one that exhibits resistance or tolerance to BDM as well as plants regenerated therefrom which may express some or all of the physiological and morphological characteristics of a disclosed sweet basil plant.

Disclosed are eight new sweet basil varieties ('Thunderstruck', 'Passion', 'Obsession', 'Rutgers Devotion DMR', '26_24_33', '50_03_05', '50_03_34', and '42_21_02'), which include a single locus conversion. The single locus conversion can include a transgenic gene which has been introduced by genetic transformation. In some embodiments, the single locus conversion can include a dominant or recessive allele. The locus conversion can confer any trait upon the single locus converted plant, including nutritional value, aromatic value, herbicide resistance, insect resistance, resistance to bacterial, fungal, or viral disease, male fertility or sterility, and improved nutritional quality.

A first generation (F1) hybrid seed produced by crossing a plant of the disclosure ('Thunderstruck', 'Passion', 'Obsession', 'Rutgers Devotion DMR', '26_24_33', '50_03_05', '50_03_34', and/or '42_21_02') to a second sweet basil plant is provided. Also provided are the F1 hybrid sweet basil plants grown from the hybrid seed produced by such crossing, and the seeds of an F1 hybrid plant. In some embodiments, the $F_1$ hybrid sweet basil plant is grown from the hybrid seed produced by crossing a new sweet basil variety provided herein ('Thunderstruck', 'Passion', 'Obsession', 'Rutgers Devotion DMR', '26_24_33', '50_03_05', '50_03_34', and '42_21_02') to a second sweet basil plant. In specific examples, provided is a seed of an $F_1$ hybrid plant produced with a new sweet basil variety provided herein as one parent, the second filial generation ($F_2$) sweet basil plant grown from the seed of the $F_1$ hybrid plant, and the seeds of the $F_2$ hybrid plant. Also provided are the development of inbred lines reaching six or more generations of selfing one or more of the 'Thunderstruck', 'Passion', 'Obsession', 'Rutgers Devotion DMR', '26_24_33', '50_03_05', '50_03_34', and '42_21_02' cultivars.

Methods of producing sweet basil seeds are provided. Such a method can include crossing a new sweet basil variety ('Thunderstruck', 'Passion', 'Obsession', 'Rutgers Devotion DMR', '26_24_33', '50_03_05', '50_03_34', and/or '42_21_02') to any second sweet basil plant, including itself or another plant of the disclosure. In particular embodiments, the method of crossing includes (a) planting seeds of a sweet basil plant provided herein; (b) cultivating sweet basil plants resulting from the seeds until said plants bear flowers; (c) allowing fertilization of the flowers of said plants; and (d) harvesting seeds produced from said plants.

In one example, methods of producing sweet basil seeds (such as hybrid seeds) include crossing a new sweet basil variety ('Thunderstruck', 'Passion', 'Obsession', 'Rutgers Devotion DMR', '26_24_33', '50_03_05', '50_03_34', 'or '42_21_02') to a second, sweet basil plant, which is nonisogenic to the new sweet basil variety. In particular examples, crossing includes cultivating sweet basil plants grown from seeds of the new variety(ies) provided herein and cultivating sweet basil plants grown from seeds of a second, distinct sweet basil plant until the plants bear flowers; cross-pollinating a flower on one of the two plants with the pollen of the other plant; and harvesting the seeds resulting from the cross pollination.

Methods for developing BDM sweet basil plants in a sweet basil breeding program are provided. Such methods can include using a plant or part thereof from a new basil variety ('Thunderstruck', 'Passion', 'Obsession', 'Rutgers Devotion DMR', '26_24_33', '50_03_05', '50_03_34', and/or '42_21_02') as a source of breeding material using plant breeding techniques, such as recurrent selection, mass selection, bulk selection, backcrossing, pedigree breeding, genetic marker-assisted selection, and genetic transformation. In certain examples, the cultivar 'Thunderstruck', 'Passion', 'Obsession', 'Rutgers Devotion DMR', '26_24_33', '50_03_05', '50_03_34', or '42_21_02' is used as a male or female parent.

Methods of producing a sweet basil plant derived from a plant provided herein ('Thunderstruck', 'Passion', 'Obsession', 'Rutgers Devotion DMR', '26_24_33', '50_03_05', '50_03_34', or '42_21_02'), such as an inbred sweet basil plant, are provided. Such methods can include (a) preparing a progeny plant derived from a plant of a new sweet basil variety ('Thunderstruck', 'Passion', 'Obsession', 'Rutgers Devotion DMR', '26_24_33', '50_03_05', '50_03_34', and '42_21_02') by crossing the plant with a second sweet basil plant; and (b) crossing the progeny plant with itself or a second plant to produce a progeny plant of a subsequent generation which is derived from a plant of a disclosed new sweet basil variety. The method can further include (c) crossing the progeny plant of a subsequent generation with itself or a second plant; and (d) repeating steps (b) and (c) for, least 2 additional generations (such as at least 3, at least 5, or at least 10 additional generations) to produce an inbred sweet basil plant derived from a plant of a new sweet basil variety provided herein.

Methods of producing a sweet basil plant derived from a new sweet basil variety 'Thunderstruck', 'Passion', 'Obsession', 'Rutgers Devotion DMR', '26_24_33', '50_03_05', '50_03_34', and '42_21_02' can include (a) crossing a derived sweet basil plant with itself or another sweet basil plant to yield additional derived progeny sweet basil seed; (b) growing the progeny sweet basil seed of step (a) under plant growth conditions to yield additional derived sweet basil plants; and (c) repeating the crossing and growing steps of (a) and (b) to generate further sweet basil plants. In specific embodiments, steps (a) and (b) may be repeated from 0 to 7 times (such as 0 to 4 or 1 to 5 times, such as 1, 2, 3, 4, or 5 or more times) as desired to generate further sweet basil plants derived from a new sweet basil variety provided herein ('Thunderstruck', 'Passion', 'Obsession', 'Rutgers Devotion DMR', '26_24_33', '50_03_05', '50_03_34', or '42_21_02').

Methods of producing sweet basil seed from a parent plant provided herein ('Thunderstruck', 'Passion', 'Obsession', 'Rutgers Devotion DMR', '26_24_33', '50_03_05', '50_03_34', and/or '42_21_02') are provided. In some examples such methods include crossing a sweet basil variety provided herein with itself or a second sweet basil plant and harvesting a resulting sweet basil seed. In some examples, the sweet basil plant has a desirable trait, which is introduced into plants in the form of seeds resulting from such a cross. For example, the second plant can be transgenic, wherein the transgene confers the desirable trait. Seeds produced by such methods, including $F_1$ hybrid seeds, as well as sweet basil plants or parts thereof produced by growing such a seed, are provided. In some examples, the method of crossing includes planting seeds of the sweet basil variety provided herein, cultivating sweet basil plants resulting from the seeds until the plants bear flowers, allowing fertilization of the flowers of the plants; and harvesting seeds produced from the plants.

Methods are provided for producing a plant of a sweet basil variety provided herein ('Thunderstruck', 'Passion', 'Obsession', 'Rutgers Devotion DMR', '26_24_33', '50_03_05', '50_03_34', and/or '42_21_02') that has one or more added desired agronomic traits, as well as plants and seeds generated from such methods. In one example, such a method provides a sweet basil plant having a single locus conversion of a sweet basil variety provided herein, wherein the sweet basil plant includes or expresses the physiological and morphological characteristics of a new sweet basil variety provided herein (such as those shown in any of Tables 3 to 9). Such methods can include introducing one or more transgenes that confer one or more desired traits into a plant of a new sweet basil variety provided herein. A transgenic or non-transgenic single locus conversion can also be introduced by backcrossing. Exemplary desired traits include herbicide tolerance or resistance, resistance or tolerance to an insect, resistance or tolerance to a bacterial disease, resistance or tolerance to a viral disease, resistance or tolerance to a fungal disease, resistance or tolerance to a nematode, resistance or tolerance to a pest, male sterility, site-specific recombination; abiotic stress tolerance (such as tolerance to drought, heat, cold, low or high soil pH level, and/or salt), modified downy mildew resistance and tolerance content, or other desired qualities.

Methods of introducing a single locus conversion (such as a desired trait) into a new sweet basil variety disclosed herein ('Thunderstruck', 'Passion', 'Obsession', 'Rutgers Devotion DMR', '26_24_33', '50_03_05', '50_03_34', and '42_21_02') are provided. In some examples the methods include (a) crossing a plant of a new sweet basil variety disclosed herein with a second plant having one or more desired traits to produce $F_1$ progeny plants; (b) selecting $F_1$ progeny plants that have the desired trait to produce selected $F_2$ progeny plants; (c) crossing the selected progeny plants with at least a first plant of 'Thunderstruck', 'Passion', 'Obsession', 'Rutgers Devotion DMR', '26_24_33', '50_03_05', '50_03_34', or '42_21_02' to produce backcross progeny plants; (d) selecting backcross progeny plants that have the desired trait and physiological and morphological characteristics of a new sweet basil variety disclosed herein to produce selected backcross progeny plants; and (e) repeating steps (c) and (d) one or more times in succession to produce selected second or higher backcross progeny plants that include the desired trait and the physiological and morphological characteristics of one of a new sweet basil variety disclosed herein when grown in the same environmental conditions. In some embodiments, the single locus confers a desirable trait, such herbicide tolerance or resistance, drought tolerance, heat tolerance, low or high soil pH level tolerance, salt tolerance, resistance or tolerance to an insect, resistance or tolerance to a bacterial disease, resistance or tolerance to a viral disease, resistance or tolerance to a fungal disease, resistance or tolerance to a nematode, resistance or tolerance to a pest, male sterility, site-specific recombination, abiotic stress tolerance (such as tolerance to drought, heat, low or high soil pH level, and/or salt), and in particular modified resistance to basil downy mildew disease, such as downy mildew resistance. In some examples, the single locus confers the ability to synthesize a protein encoded by a gene located within the single locus.

The disclosure also provides sweet basil plants and parts thereof produced by any of the methods disclosed herein. In some embodiments, sweet basil plants produced by the disclosed methods includes at least two, at least three, at least four, at least five, or at least 10 of the traits of a new sweet basil variety as described herein. In some embodiments, the sweet basil plants produced by the disclosed methods include at least two, at least three, at least four, at least five, or at least 10 of the traits of a new sweet basil variety provided herein (see Tables 3 to 9), such as providing downy mildew resistance and/or conferring a degree of high tolerance under high disease pressure of downy mildew, as described herein.

The disclosure provides sweet basil seed deposited as ATCC Accession No. PTA-124576, PTA-124574, PTA-124572, PTA-124578, PTA-124575, PTA-124573, PTA-124571, and PTA-124577.

Methods are provided for producing and using an extract or an essential oil from the new sweet basil variety provided herein. For example, such an extract or essential oil can be used in foods, flavors, fragrances and other products.

Also provided herein is packaging material containing one or more 'Thunderstruck', 'Passion', 'Obsession', 'Rutgers Devotion DMR', '26_24_33', '50_03_05', '50_03_34', or '42_21_02' plants or parts thereof (such as biomass, leaves, extract, and/or oil(s)). In some examples, such a package includes cells, DNA, and/or protein from a 'Thunderstruck', 'Passion', 'Obsession', 'Rutgers Devotion DMR', '26_24_33', '50_03_05', '50_03_34', and/or '42_21_02' cultivar. Exemplary packaging material includes, but is not limited to, boxes, bags, plastic containers, bottles, jars, or other containers. Such packaging material can be made from glass, paper, or plastic.

For example, the disclosure provides a package containing a plant or part thereof from one or more of 'Thunderstruck', 'Passion', 'Obsession', 'Rutgers Devotion DMR', '26_24_33', '50_03_05', '50_03_34', and '42_21_02' (such as a bag, jar, box, bottle, or other container containing leaves and/or biomass from 'Thunderstruck', 'Passion', 'Obsession', 'Rutgers Devotion DMR', '26_24_33', '50_03_05', '50_03_34', and/or '42_21_02'). In some examples, the leaves and/or biomass are dried or freeze dried. In some examples, the leaves and/or biomass are frozen. In some examples, the leaves and/or biomass are fresh. The leaves and/or biomass of 'Thunderstruck', 'Passion', 'Obsession', 'Rutgers Devotion DMR', '26_24_33', '50_03_05', '50_03_34', '42_21_02' and/or '42_21_02' may be combined with leaves and/or biomass of other sweet basil varieties, or other materials (such as other herbs, such as oregano leaves, parsley leaves, and/or other basils apart from the disclosed sweet basils, and the like). In one example, a plant or part thereof from one or more of 'Thunderstruck', 'Passion', 'Obsession', 'Rutgers Devotion DMR', '26_24_33', '50_03_05', '50_03_34', and '42_21_02' (such as biomass or leaves) are part of a food or fragrance product.

An essential oil extract from one or more of 'Thunderstruck', 'Passion', 'Obsession', 'Rutgers Devotion DMR', '26_24_33', '50_03_05', '50_03_34', and '42_21_02' also provided. In one example, the oil extract includes an aromatic oil characterized as a sweet basil containing linalool, methyl chavicol, 1-8, cineole and other aromatic constituents in ratios that impart a sweet basil aroma. In some examples, such an extract includes DNA and/or protein from a 'Thunderstruck', 'Passion', 'Obsession', 'Rutgers Devotion DMR', '26_24_33', '50_03_05', '50_03_34', and '42_21_02' cultivar.

Also provided are methods of using either parent variety ('Mrihani' and/or 'SB22', ATCC Accession Nos. 124616 and 124617, respectively) in a breeding program, for example to produce a sweet basil plant resistant to *Peronospora belbahrii*. In some examples, the method includes crossing non-sweet basil variety 'Mrihani' (MRI) with sweet basil variety 'SB22', thereby generating a sweet basil plant resist to *Peronospora belbahrii*. In some examples, the method includes crossing non-sweet basil variety 'Mrihani' with a sweet basil variety to generate a sweet basil plant resist to *Peronospora belbahrii*. In some examples, the method includes crossing sweet basil variety 'SB22' with a different sweet basil variety to generate a sweet basil plant resist to *Peronospora belbahrii*. Progeny and seed (such as $F_1$ progeny and seed) produced from such crosses are provided herein. Also provided are plants and parts thereof resulting from such crosses, such as from $F_1$ progeny and/or seed. Such plants (and parts thereof, such as oils and leaves) and seeds, can be used in the disclosed compositions and methods. Also provided are genetically modified versions of 'Mrihani' and 'SB22', such as those that include one or more transgenes that confer a desirable trait, such as one or more of those provided herein. In one example, the 'Mrihani' or 'SB22', variety is modified using gene editing (such as gene silencing).

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SEQUENCE LISTING

Figure 1:
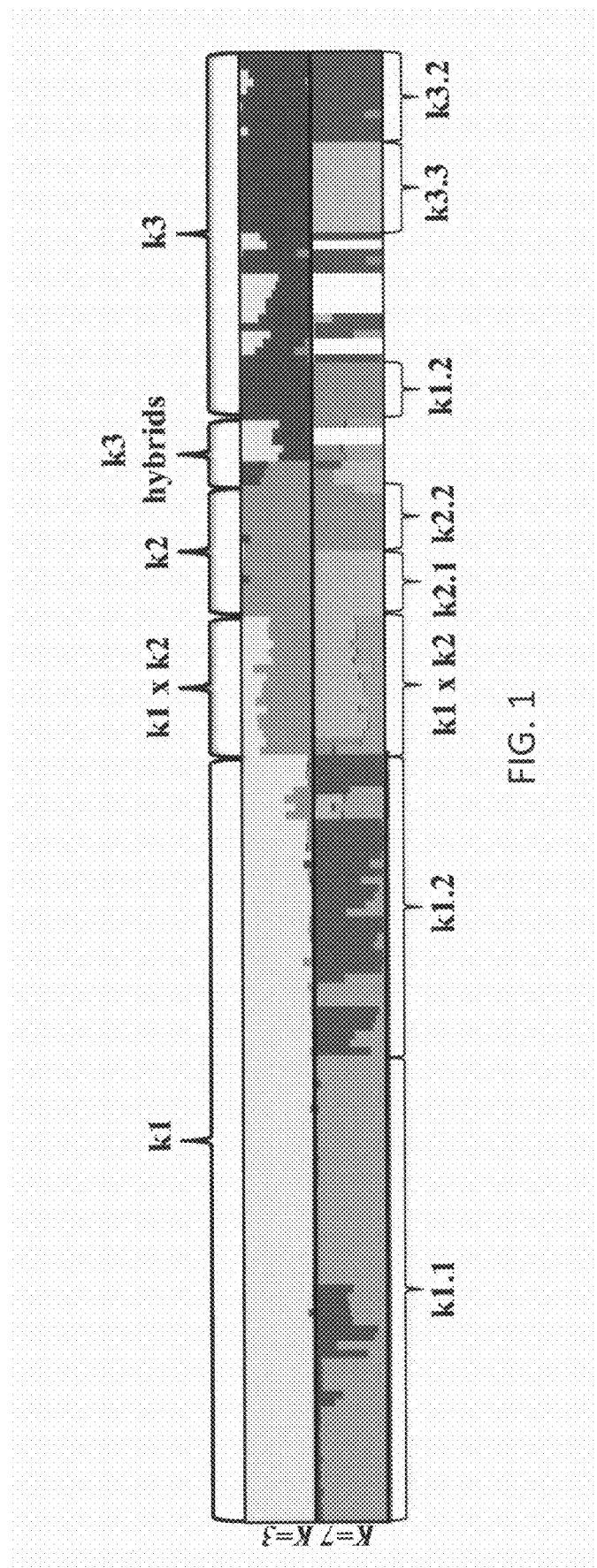
FIG. 1. Primary and nested population structure for 180-accession panel of *Ocimum* species. Primary and secondary (nested) model-based clustering analysis using Structure ver 2.2.3 software for panels of *Ocimum* spp. accessions using 20 EST-SSR markers. Major clusters (K=3) (top histogram) and sub-clusters (K=7) (bottom histogram) derived from primary and nested clustering iterations. Ten accessions were admixed and nested population structure could not be inferred due to unknown parentage of admixed primary cluster membership (white bars).

The nucleic sequences are shown using standard letter abbreviations for nucleotide bases, as defined in 37 C.F.R. 1.822. Only one strand of each nucleic acid sequence is shown, but the complementary strand is understood as included by any reference to the displayed strand. The sequence listing generated on Oct. 31, 2017 16 Kb, and submitted herewith, is herein incorporated by reference.

SEQ ID NOS: 1-58 are SSR primer sequences used for genotyping.

SEQ ID NO: 59 is a nucleic acid sequence attached to the 5'end of each of forward primer in Table 10 to facilitate fluorescent labeling of PCR products.

DETAILED DESCRIPTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a plant" includes one or a plurality of such plants. The term "or" refers to a single element of stated alternative elements or a combination of two or more elements, unless the context clearly indicates otherwise. For example, the phrase "A or B" refers to A, B, or a combination of both A and B. Furthermore, the various elements, features and steps discussed herein, as well as other known equivalents for each such element, feature or step, can be mixed and matched by one of ordinary skill in this art to perform methods in accordance with principles described herein. Among the various elements, features, and steps some will be specifically included and others specifically excluded in particular examples.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. All references cited herein are incorporated by reference in their entirety.

In some examples, the numbers expressing quantities of ingredients, properties such as molecular weight, reaction conditions, and so forth, used to describe and claim certain embodiments are to be understood as being modified in some instances by the term "about" or "approximately." For example, "about" or "approximately" can indicate +/−20% variation of the value it describes. Accordingly, in some embodiments, the numerical parameters set forth herein are approximations that can vary depending upon the desired properties sought to be obtained by a particular embodiment. Notwithstanding that the numerical ranges and parameters setting forth the broad scope of some examples are approximations, the numerical values set forth in the specific examples are reported as precisely as practicable. The recitation of ranges of values herein is merely intended to serve as a shorthand method of referring individually to each separate value falling within the range.

Backcross: The mating of a hybrid to one of its parents. For example hybrid progeny, for example a first generation hybrid ($F_1$), can be crossed back one or more times to one of its parents. Backcrossing can be used to introduce one or more single locus conversions (such as one or more desirable traits) from one genetic background into another.

Basil downy mildew (BDM): The pathogen *Peronospora belbahrii* responsible for causing downy mildew in basil plants. Initial symptoms usually include yellow areas visible on the upper leaf surface often confined within the veins of the leaf. In situations of high disease pressure brought about by very increased levels of pathogen spores in the crop canopy brown to black leaf lesions resulting from cell death appear and may expand.

The spectrum of resistance through susceptibility to BDM can be measured by sporulation as opposed to leaf yellowing, which may be the result of extenuating factors such as nitrogen deficiency. Thus, response can be measured on the basis of % sporulation. In one example a scale from 0 to 4 is used, comparing all genotypes in a given test (0=no sporulation, 1=1% to 10% sporulation, 2=11% to 25% sporulation, 3=26% to 50% sporulation, and 4=51% to 100% sporulation). This scale facilitates rapid scoring of multiple leaves from individual plants or plots of multiple plants (i.e. homogenous varieties or breeding lines), while providing a repeatable and representative measure of disease reaction on an individual plant basis. For selection of individual plants, six mature leaves are detached from each plant and assigned a score from which a DSI was calculated on a single-plant basis using the equation:

$$DSI = \frac{\sum (\text{single leaf} \times \text{disease rating})}{(\text{number of leaves scored} \times \text{maximum disease rating})}$$

For isogenic varieties or breeding lines replicated plots, typically between 10-15 feet, are assigned a score based on the aggregate level of sporulation among plants. In this case disease severity can be reported as the mean score across replicated plots on a given date or scoring dates can be combined and used to calculate area under the disease progress curve (AUDPC) (see Table 6).

As used herein, "resistance" to BDM is used to describe plants for which sporulation over the growing season or cycle of the plant has not been observed in any environment and across all levels of disease pressure including the most severe.

As used herein, "tolerance" to BDM is used to describe plants exhibiting some degree of symptoms and/or sporulation that does not preclude its sale in the marketplace. Thus, total yield may decrease but not the extent of significant economic impact with regard to the sale of the product. BDM tolerance can vary according to the number and nature of genes conferring the host response. BDM tolerance can also be subject to interaction with the environment, which directly affects the level of disease pressure and will vary under different environmental conditions, inoculum density, plant age and length of season. Nevertheless, the disclosed new sweet basil varieties have exhibited under field conditions no-to-few BDM symptoms, depending upon when the rating occurs, and are referred to herein a BDM resistant/tolerant. In addition, each new variety significantly outperformed commercial controls to which they have been compared relative to the expression of BDM on the susceptible control sweet basils and the absence to few signs of BDM on these new sweet basils (see Table 6).

All of the disclosed new sweet basil varieties ('Thunderstruck', 'Passion', 'Obsession', 'Rutgers Devotion DMR', '26_24_33', '50_03_05', '50_03_34', and '42_21_02') are at least or less sporulation during the growing cycle, but may demonstrate minor differences in response by environments due to absence or presence of minor QTL. Across environments these varieties have significantly higher tolerance then any known culinary sweet basil variety commercially available.

Biomass: Organic matter derived from an organism, such as a sweet basil plant or part thereof. In some examples, biomass refers to all the above ground plant material at a particular point of time, thus including the leaves, stems and may include flowers (at varying stages of development given the flowering period ranges over a period of time). Biomass can include all vegetative and reproductive material produced by the plant at time of harvest.

Cell. Cell as used herein includes a plant cell, whether isolated, in tissue culture or incorporated in a plant or plant part.

Cross. Synonymous with hybridize or crossbreed. Includes the mating of genetically different individual plants, such as the mating of two parent plants.

Cross-pollination: Fertilization by the union of two gametes from different plants.

Essential oil (EO): A concentrated hydrophobic liquid containing volatile aroma compounds from aromatic plants, such as a sweet basil plant. An oil is "essential" in the sense that it historically was considered by some to be the "essence of" the plant's fragrance; it does not mean indispensable. The essential oil of sweet basil accumulates in glandular trichomes in leaves and flowers of the sweet basil plant and these compounds impart the characteristic aroma/odor of aromatic plants/culinary herbs including sweet basil. Methods of generating or obtaining an EO from a plant include extraction by distillation (e.g., by using steam or water or combination), expression, solvent extraction, absolute oil extraction, super critical fluid extraction, cold pressing, or combinations thereof. Methods may also include capturing such aromas that are naturally volatizing from the plant using static or nonstatic headspace above the plant material in an enclosed vial or chamber from which the volatiles are then captured.

$F_1$ hybrid: The first generation progeny of the cross of two stable parents that are nonisogenic or isogenic plants.

Gene Silencing. A general term describing epigenetic processes of gene regulation, including any technique or mechanism in which the expression of a gene is prevented.

Genotype. The genetic constitution of a cell, an organism, or an individual (i.e., the specific allele makeup of the individual) usually with reference to a specific character under consideration.

Plant: Includes reference to an immature or mature whole plant, including a plant from which seed, roots or leaves have been removed. Seed or embryo that will produce the plant is also considered to be the plant.

Plant parts. Includes protoplasts, leaves, stems, roots, root tips, anthers, pistils, seed, embryo, pollen, ovules, cotyledon, hypocotyl, flower, shoot, tissue, petiole, cells, meristematic cells and the like. Includes plant cells of a tissue culture from which Sweet basil plants can be regenerated.

Progeny. Offspring; descendants.

Regeneration. The development of a plant from tissue culture. The cells may, or may, not have been genetically modified. Plant tissue culture relies on the fact that all plant cells have the ability to generate a whole plant (totipotency). Single cells (protoplasts), pieces of leaves, or roots can often be used to generate a new plant on culture media given the required nutrients and plant hormones.

Self-pollination: The transfer of pollen from the anther to the stigma of the same plant.

Single locus converted (conversion) plant: Plants developed by backcrossing and/or by genetic transformation, wherein essentially all of the desired morphological and physiological characteristics of a sweet basil variety are recovered in addition to the characteristics of the single locus transferred into the variety via the backcrossing technique and/or by genetic transformation.

Sweet basil: As used herein, sweet basil (*Ocimum basilicum*) or sometimes referred to as American Basil, French Basil, Italian Basil refers to any plant from the genus and species *Ocimum basilicum*. As used herein, sweet basil may also refer to a variant, progeny, or offspring of such a plant, including a plant or part thereof. The terms variety, cultivar, or the like may be used interchangeably to refer to a plant of the present disclosure.

Tissue culture: A composition that includes isolated cells of the same or a different type or a collection of such cells organized into parts of a plant.

Transformation. The introduction of new genetic material (e.g., exogenous transgenes) into plant cells. Exemplary mechanisms that are to transfer DNA into plant cells include (but not limited to) electroporation, microprojectile bombardment, *Agrobacterium*-mediated transformation and direct DNA uptake by protoplasts.

Transgene. A gene or genetic material that has been transferred into the genome of a plant, for example by genetic engineering methods. Exemplary transgenes include cDNA (complementary DNA) segment, which is a copy of mRNA (messenger RNA), and the gene itself residing in its original region of genomic DNA. In one example, describes a segment of DNA containing a gene sequence that is introduced into the genome of a sweet basil plant or plant cell. This non-native segment of DNA may retain the ability to produce RNA or protein in the transgenic plant, or it may alter the normal function of the transgenic plant's genetic code. In general, the transferred nucleic acid is incorporated into the plant's germ line. Transgene can also describe any DNA sequence, regardless of whether it contains a gene coding sequence or it has been artificially constructed, which has been introduced into a plant or vector construct in which it was previously not found.

New Downy Mildew Resistant/Tolerant Sweet Basil Cultivars

The impact of BDM has impacted traditional basil seed producing regions (e.g., Italy, Kenya, Europe, USA) to such an extent that seedstock can no longer be grown in these locations when the disease is present as commercial sweet basils are susceptible. The rapid spread of BDM in basil producing regions around the world in the absence of effective genetic resistance and poor chemical control measures have resulted in significant crop failures and limited shelf life. In response to the threat of BDM, the inventors developed and identified several new BDM resistant/tolerant basil genotypes from the sweet basil species (*Ocimum basilicum* L.). Although multiple years of field experiments indicate that adoption of a diligent schedule of chemical applications can reduce the impact of BDM (Homa et al., Plant Dis. 89:1561-1566, 2014; Wyenandt et al., Phytopathology 105:885-894, 2015), the extent to which disease severity is reduced is difficult to justify economically by the cost of chemical applications for this burgeoning yet minor specialty crop. In addition, under organic production systems, adequate control measures have not been effective, putting the organic basil acreage in the US and abroad at risk for significant losses.

To generate the disclosed new BDM resistant/tolerant basil varieties ('Thunderstruck', 'Passion', 'Obsession', 'Rutgers Devotion DMR', '26_24_33', '50_03_05', '50_03_34', and '42_21_02'), the sweet basil 'Mrihani' (unpatented) was selected after extensive screening of commercially available sweet basils, nonsweet basils and exotic basils to identify possible sources of resistance as an appropriate donor for introduction of BMD resistance/tolerance genes by a pedigree selection strategy informed by investigation of the genes mediating 'Mrihani'-conferred BDM response. Adoption of this strategy facilitated development of an inbred family of sweet basil varieties that are resistant or highly tolerant to BDM. The new varieties were derived from a single source of resistance which led to the creation of eight new distinct sweet basil cultivars with different plant phenotypes. According to phylogenetic analysis, DM resistant genotypes are ubiquitous outside the *O. basilicum* species; however, the phenotype and chemotype of those *Ocimum* spp. precludes their use in commercial sweet basil markets as they neither appear visually to look like any type of edible sweet basil nor smell and taste like anything closely related to a sweet basil. Thus, there are currently no commercially available sweet basils with sufficient tolerance to BDM. Basil cultivars with BDM resistance/tolerance are critically needed given that the majority of US production acreage remains at-risk to this disease, particularly for the organic producers where even less successful management options are available.

Plant breeding programs evaluate available genotypes (germplasm) for primary traits of interest (e.g., disease resistance) and characterization of their genetic relatedness. Therefore, preliminary efforts in identifying BDM resistant/tolerant varieties included high-throughput BDM response evaluations of >200 basil accessions and phylogenetic analysis of >170 basil accessions facilitated by the development of high quality EST-SSR markers (FIG. 1). Population structure analysis revealed three major demarcations of genetic similarity or groups (k1, k2 and k3) and seven sub-groups (k1.1, k1.2, k2.1, k2.2, k3.1, k3.2, k3.3). The major k1 group includes 94 *O. basilicum* genotypes that include the k1.1 commercial sweet basil sub-group. Efforts to introduce resistance from k2 and k3 were made through hybridization (k1×k2 and k3 hybrid), but $F_1$ sterility prevented further breeding efforts. However, a single genotype, 'Mrihani', located in the k1 group was identified providing a source of BDM resistance/tolerance, given its sexual compatibility with commercial sweet basil k1.1 sub-group.

A six-generation, full-sibling family developed from a cross between 'Mrihani' (also referred to herein as MRI) (an *Ocimum basilicum* non-sweet basil phenotype) and inbred breeding line 'SB22' (unpatented) (a sweet basil phenotype (Large-leaf Italian phenotype) with basil *Fusarium* wilt tolerance (FOB)), indicated DM resistance was mediated by major gene control (Pyne et al., *J. Amer. Soc. Hort. Sci.* 140:396-403, 2015). The $F_2$ generation was subsequently genotyped using 1,847 double digestion restriction site associated DNA sequencing (ddRADseq) single nucleotide polymorphism (SNP) and 42 expressed sequence tag (EST)-SSR DNA markers. These markers were employed in the creation of a genetic map for sweet basil. Quantitative trait loci (QTL) analysis detected a genomic region on linkage group (LG) 11 demonstrating significant (p<0.001) association with MRI-conferred BDM resistance. Two additional "minor" QTL detected on LGs 9 and 14 had an impact dependent upon environment.

Based on these results, a pedigree selection method was used to develop advanced breeding material that are stable for BDM resistance/tolerance, and have the proper flavor, aromas, leaf shape (phenotype), biomass production, and other traits needed for commercial marketability.

The present disclosure provides a series of new basil downy mildew resistant (DMR) sweet basil cultivars ('Thunderstruck', 'Passion', 'Obsession', 'Rutgers Devotion DMR', '26_24_33', '50_03_05', '50_03_34', and '42_21_02') derived from a series of crosses and selections between, 'Mrihani' with 'SB22'. The eight new distinct sweet basil cultivars are each tolerant to *Peronospora belbahrii*, the causal agent of BDM in *Ocimum* spp. and are significantly more tolerant than all other commercial sweet basils in the marketplace or commercially available. This BDM tolerance and/or resistance trait results in sweet basil cultivars that are distinct from all other sweet basils currently on the commercial market. While there have been sweet basil varieties and some other basils have been described as having BDM tolerance in commercial seed catalogs, the inventors observed that none of the sweet basils available were resistant and under field conditions, exhibited severe BDM symptoms and were significantly less tolerant to BDM than the eight sweet basils described herein. In some cases in New Jersey and Florida, those commercial cultivars died from BDM while the new varieties thrived despite the presence of BDM under ambient conditions.

A series of selected progeny resulted from crossing and selection over multiple generations (n=8). BDM response evaluations were performed under controlled greenhouse and field-environments subjected to appropriate inoculum densities of BDM inoculum pressure. Procedures used to evaluate response to BDM are described for the field (Wyenandt et al., Phytopathology 105:885-894, 2010; Wyenandt et al., HortScience 45(9): 1416-1419, 2015) and greenhouse (Pyne et al., *HortSci* 49:1041-5, 2014). Repeated evaluations led to the discovery of a series of sweet basil inbred lines having BDM resistance/tolerance in addition to the visual appearances, flavor and aromas desired for the traditional sweet basil market. These new cultivars are genetically stable or pure conferring uniformity generation to generation from seed as well as from clonal/vegetative propagation. Genetic fingerprinting of these new eight varieties confirms their phenotypic homogeneity and facilitates their identification from other commercial sweet basil varieties. These new cultivars (e.g., seeds, plants, and parts thereof) can be used for the fresh, processing, fresh frozen, ornamental, and heath markets for growers, processors and horticulturalists/home gardeners.

In some examples, currently commercially available sweet basils are damaged by BDM by about 15%-100% leading to crop loss and plant death. In contrast, the disclosed new varieties only exhibit <10% damage when subjected to the same levels of disease pressure during representative growth periods (prior to the flowering growth stages) in the absence of commercial fungicide and other chemical control agents used to suppress BDM. In some examples, the use of these new sweet basil varieties provide all season control during short or long seasons in tropical, sub-tropical, and temperate growing regions.

The new sweet basils ('Thunderstruck', 'Passion', 'Obsession', 'Rutgers Devotion DMR', '26_24_33', '50_03_05', '50_03_34', and '42_21_02') were developed to be resistant to or highly tolerant to BDM for commercial agricultural production and home gardens. These varieties, as well as their progeny, can be grown in the open fields or high tunnels, in greenhouses in pots or other containers, hydroponically, aeroponically, or produced in any manner that when exposed to ambient levels of BDM will still produce a marketable fresh or dried or processed product with no-to-few signs/symptoms of BDM depending upon disease pressure. In comparison to all other current commercial varieties, when under mild, moderate, or high DM pressure, these new varieties outperform all other comparable commercially-available sweet basils in all manners related to commercial production, including growth and development and biomass production due to their BDM resistance/tolerance (Table 6). The present disclosure provides sweet basil plants with increased BDM resistance/tolerance relative to a wild type sweet basil plant and relative to other commercially available sweet basils.

The new sweet basil plants also exhibit an aroma and flavor characteristic of sweet basil. In addition to human sensory responses, chemical characterization of the essential oil of these plants using both gas chromatography (GC) and mass spectroscopy (MS) confirmed that the aroma is characteristic of sweet basil (Lee et al., Perfumer & Flavorist 42:37-40,42-50, 2017) used in the fresh market (see FIG. 5 and Table 7-9). In comparison, other specialized basils have characteristic aromas of camphor, lemon, lime, or cinnamon, not accepted as sweet basil. For example, the aroma of traditional, 'Italian' basil can be described by the relative concentrations of only a few major volatile constituents: linalool, methyl chavicol, 1,8 cineole and eugenol. In some examples, extracted essential oil of a disclosed sweet basil variety contains 50-70% linalool (or less) and does not exceed 30% methyl chavicol. Thus, the new sweet basil cultivars 'Thunderstruck', 'Passion', 'Obsession', 'Rutgers Devotion DMR', '26_24_33', '50_03_05', '50_03_34', and '42_21_02' and progeny thereof can be used in the production of fresh and/or dried sweet basil, or for the distilled aromatic essential oils, which have multiple applications in foods, flavors, fragrances, nutraceuticals, and culinary herbs.

Figures 2A, 2B:
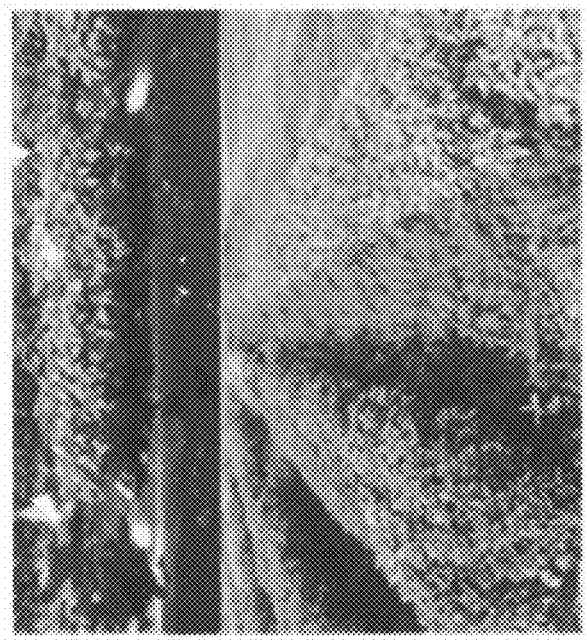
FIGS. 2A-2B. Images of DMR lines during two phases of breeding. (A) BDM tolerance observed in the University of Florida, Everglades Research & Education Center, Belle Glade, Fla. Small plants designated with yellow dots indicate commercial controls which exhibit the BDM and are each close to death, remaining plants in the middle and between the yellow painted dots on the plastic mulch are full-siblings of cross 469-11/SB13. (B) subsequent field evaluation in which progeny have been stabilized from single seed descent and demonstrate a uniform tolerance response (left) versus susceptibility of the commercial sweet basil control (right), photograph taken at the Rutgers University Clifford E & Melda C. Snyder Research and Extension Farms, near Pittstown, N.J.

Thus, provided herein are seeds of new sweet basil cultivars 'Thunderstruck', 'Passion', 'Obsession', 'Rutgers Devotion DMR', '26_24_33', '50_03_05', '50_03_34', and '42_21_02', wherein representative sample seed of the varieties are deposited under ATCC Accession Numbers: PTA-124576, PTA-124574, PTA-124572, PTA-124578, PTA-124575, PTA-124573, PTA-124571, and PTA-124577, respectively. The disclosure provides sweet basil plants having or consisting of the morphological and physiological characteristics of the new sweet basil varieties provided herein. The disclosure also provides sweet basil plants having one or more of the morphological and physiological characteristics of the new sweet basils (such as those shown in FIGS. 2, 4, 5 and Tables 3 to 9). Also provided are seeds of such plants, progeny of such plants, parts of such plants (such as pollen, ovules and cells), and vegetative sprigs or clones of such plants. In one example, the disclosure provides sweet basil plants having the genotype of one or more of the new sweet basils provided herein. For example, the disclosure provides plants produced by growing the seed of a new sweet basil variety provided herein.

The disclosed new sweet basil varieties and seeds can be used to produce other sweet basil plants and seeds, for example as part of a breeding program. Choice of breeding or selection methods using to generate new sweet basil plants and seeds can depend on the mode of plant reproduction, the heritability of the trait(s) being improved, and the type of variety used commercially (e.g., $F_1$ hybrid variety, pure line variety, etc.). For highly heritable traits, a choice of superior individual plants evaluated at a single location can be effective, whereas for traits with low heritability, selection can be based on mean values obtained from replicated evaluations of families of related plants. Exemplary selection methods commonly include pedigree selection, modified pedigree selection, mass selection, recurrent selection and backcrossing.

The complexity of inheritance influences choice of the breeding method. Backcross breeding can be used to transfer one or a few favorable genes for a highly heritable trait into a desirable variety. This approach has been used extensively for breeding disease-resistant varieties (e.g., see Bowers et al., 1992. Crop Sci. 32(1):67-72; Nickell and Bernard, 1992. Crop Sci. 32(3):835). Various recurrent selection techniques can be used to improve quantitatively inherited traits controlled by numerous genes.

Promising advanced breeding lines can be thoroughly tested and compared to appropriate standards in environments representative of the commercial target area(s) for generally two or more years in multiple locations. The best or most preferred lines are candidates for new commercial varieties. Those still deficient in a few traits may be used as parents to produce new populations for further selection.

One method of identifying a superior plant is to observe its performance relative to other experimental plants and to one or more widely grown standard varieties.

Plant breeding can result in new, unique and superior sweet basil varieties and hybrids from a disclosed new sweet basil variety. Two or more parental lines can be selected (such as one or more of new sweet basil cultivars 'Thunderstruck', 'Passion', 'Obsession', 'Rutgers Devotion DMR', '26_24_33', '50_03_05', '50_03_34', and '42_21_02'), followed by repeated selfing and selection, producing many new genetic combinations. Each year, the germplasm to advance to the next generation is selected. This germplasm is grown under unique and different geographical, climatic and soil conditions, and further selections are then made, during and at the end of the growing season.

The development of new sweet basil varieties from new sweet basil cultivars 'Thunderstruck', 'Passion', 'Obsession', 'Rutgers Devotion DMR', '26_24_33', '50_03_05', '50_03_34', and '42_21_02' involves the development, identification, and selection of promising/interesting sweet basil varieties with desirable traits/characteristics, the continued growing out of those selections and elimination of those not meeting criteria of the plant developer and/or as needed the crossing of these varieties and selection of progeny from the superior hybrid crosses. A hybrid seed is produced by manual crosses between selected male-fertile parents or by using male sterility systems. Hybrids can be identified by using certain single locus traits such as flower color, pubescence color or herbicide resistance which indicate that the seed is truly a hybrid. Additional data on parental lines as well as the phenotype of the hybrid can influence a decision whether to continue with the specific hybrid cross.

Pedigree breeding and recurrent selection breeding methods can be used to develop varieties from breeding populations. Breeding programs combine desirable traits from two or more varieties or various broad-based sources into breeding pools from which varieties are developed by selfing and selection of desired phenotypes. Pedigree breeding is commonly used for the improvement of self-pollinating crops. Two parents (e.g., wherein one of the parents is one of the new varieties provided herein), which possess favorable, complementary traits, are crossed to produce an $F_1$. An F2 population is produced by selfing one or several $F_1$'s. Selection of the best or most preferred individuals can begin in the $F_2$ population (or later depending upon the breeding objectives); then, beginning in the $F_3$, the best or most preferred individuals in the best families can be selected. Replicated testing of families can begin in the $F_3$ or $F_4$ generation to improve the effectiveness of selection for traits with low heritability. At an advanced stage of inbreeding (e.g., $F_6$ and $F_7$), the best lines or mixtures of phenotypically similar lines can be tested for potential commercial release as new varieties.

Mass and recurrent selections can be used to improve populations of either self- or cross-pollinating crops. A genetically variable population of heterozygous individuals is either identified or created by intercrossing several different parents. The best or most preferred plants are selected based on individual superiority, outstanding progeny, or excellent combining ability. The selected plants are intercrossed to produce a new population in which further cycles of selection are continued.

Backcross breeding has been used to transfer genetic loci for simply inherited, highly heritable traits into a desirable homozygous variety, which is the recurrent parent (e.g., the new variety disclosed herein). The source of the trait to be transferred is called the donor or nonrecurring parent. The resulting plant is typically expected to have the attributes of the recurrent parent (e.g., variety) and the desirable trait transferred from the donor parent. After the initial cross, individuals possessing the phenotype of the donor parent are selected and repeatedly crossed (backcrossed) to the recurrent parent. The resulting plant is typically expected to have the attributes of the recurrent parent (e.g., variety) and the desirable trait transferred from the donor parent.

The single-seed descent procedure can refer to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, a progeny represents not all of the F2 plants originally sampled in the population when generation advance is completed.

In a multiple-seed procedure, one or more seeds from each plant in a population are commonly harvested and threshed together to form a bulk. Part of the bulk is used to plant the next generation and part is put in reserve. The multiple-seed procedure makes it possible to plant the same number of seeds of a population each generation of inbreeding. Sufficient numbers of seeds are harvested to make up for those plants that did not germinate or produce seed.

Descriptions of other breeding methods that used for different traits and crops can be found in one of several reference books (e.g., Allard. 1960. Principles of plant breeding. Davis, California: John Wiley & Sons, NY, University of California, pp. 50-98; Simmonds. 1979. Principles of crop improvement. New York: Longman, Inc., pp. 369-399; Sneep and Hendriksen. 1979. "Plant breeding perspectives." Wageningen (ed.), Center for Agricultural Publishing and Documentation; Fehr. 1987).

Breeding New Sweet Basil Varieties with BDM Resistance/Tolerance

Methods for crossing one or more of the new sweet basil varieties 'Thunderstruck', 'Passion', 'Obsession', 'Rutgers Devotion DMR', '26_24_33', '50_03_05', '50_03_34', and '42_21_02' provided herein with itself or a second plant are provided, as are the seeds and plants produced by such methods. Such methods can be used for propagation of a new sweet basil variety provided herein, or can be used to produce hybrid sweet basil seeds and the plants grown therefrom. Hybrid sweet basil plants can be used, for example, in the commercial production of sweet basil products (including leaves, biomass and extracts) or in breeding programs for the production of novel sweet basil varieties. A hybrid plant can also be used as a recurrent parent at any given stage in a backcrossing protocol during the production of a single locus conversion (for example introduction of one or more desirable traits) of a new sweet basil variety provided herein.

Methods of producing sweet basil plants and/or seed are provided. Such methods can include crossing one or more of the new sweet basil varieties 'Thunderstruck', 'Passion', 'Obsession', 'Rutgers Devotion DMR', '26_24_33', '50_03_05', '50_03_34', and '42_21_02' provided herein with itself or a second sweet basil plant and harvesting a resulting sweet basil seed, such as an $F_1$ hybrid seed. The resulting plant can be grown, resulting in a sweet basil plant or part thereof.

In one example methods of producing an inbred sweet basil plant derived from a new sweet basil variety provided herein (e.g., 'Thunderstruck', 'Passion', 'Obsession', 'Rutgers Devotion DMR', '26_24_33', '50_03_05', '50_03_34', and '42_21_02') are provided. In one example such methods include (a) generating a progeny plant derived from a new sweet basil variety provided herein by crossing a plant of the new variety with a sweet basil plant of a second variety; (b) crossing the progeny plant with itself or a second plant to produce a seed of a progeny plant of a subsequent generation; (c) growing a progeny plant of a subsequent generation from said seed and crossing the progeny plant of a subsequent generation with itself or a second plant; and (d) repeating steps (b) and (c) for an additional at least 2 generations (such as at least 3, at least 4, at least 5, at least 6, at least 7, at least 8 at least 9, at least 10, at least 15 or at least 20, such as 2 to 10, 3 to 10, or 3 to 15 generations) with sufficient inbreeding to produce an inbred sweet basil plant derived from a new sweet basil variety provided herein.

The second plant crossed with a new sweet basil variety provided herein (e.g., 'Thunderstruck', 'Passion', 'Obsession', 'Rutgers Devotion DMR', '26_24_33', '50_03_05', '50_03_34', and '42_21_02') for the purpose of developing novel sweet basil varieties, is typically a plant which either themselves exhibit one or more desirable characteristics or which exhibit one or more desired characteristic(s) when in hybrid combination. In one example, the second sweet basil plant is transgenic. Exemplary desired characteristics include, but are not limited to: increased seed yield, increased seedling vigor, modified maturity date, desired plant height, high anthocyanin content, high phenolic content, herbicide tolerance or resistance, drought tolerance or resistance, heat tolerance or resistance, low or high soil pH level tolerance, salt tolerance or resistance, resistance to an insect, resistance to a bacterial disease, resistance to a viral disease, resistance to a fungal disease, resistance to a nematode, resistance to a pest, male sterility, site-specific recombination, abiotic stress tolerance, and increased BDM tolerance and/or resistance.

When a new sweet basil variety provided herein is crossed with another different variety, first generation ($F_1$) sweet basil progeny are produced. The hybrid progeny are produced regardless of characteristics of the two varieties produced. As such, an $F_1$ hybrid sweet basil plant can be produced by crossing a sweet basil variety provided herein with any second sweet basil plant. The second sweet basil plant can be genetically homogeneous (e.g., inbred) or can itself be a hybrid. Therefore the disclosure provides any $F_1$ hybrid sweet basil plant produced by crossing a new sweet basil variety provided herein with a second sweet basil plant (such as a transgenic plant having one or more genes that confer to the plant one or more desired characteristics).

Sweet basil plants can be crossed by either natural or mechanical techniques. Natural pollination occurs in sweet basil either by self-pollination or natural cross pollination, which typically is aided by pollinating organisms. In either natural or artificial crosses, flowering and flowering time can be a consideration.

Sensitivity to day length can be a consideration when genotypes are grown outside of their area of adaptation. When genotypes adapted to tropical latitudes are grown in the field at higher latitudes, they may not mature before frost occurs. Plants can be induced to flower and mature earlier by creating artificially short days or by grafting. Sweet basil plants can be grown in winter nurseries located at sea level in tropical latitudes where day lengths are shorter than their critical photoperiod. The short day lengths and warm temperatures encourage early flowering and seed maturation. Early flowering can be useful for generation advance when only a few self-pollinated seeds per plant are desired, but usually not for artificial hybridization because the flowers self-pollinate before they are large enough to manipulate for hybridization. Artificial lighting can be used to extend the natural day length to about 14.5 hours to obtain flowers suitable for hybridization and to increase yields of self-pollinated seed. The effect of a short photoperiod on flowering and seed yield can be partly offset by altitude. At tropical latitudes, varieties adapted to the northern U.S. perform more like those adapted to the southern U.S. at high altitudes than they do at sea level. The light level for delay of flowering can be dependent on the quality of light emitted from the source and the genotype being grown. For example, blue light with a wavelength of about 480 nm typically needs more than about 30 times the energy to inhibit flowering as red light with a wavelength of about 640 nm (Parker et al. 1946. *Bot. Gaz.* 108:1-26).

Temperature can also affect the flowering and development of plants. It can influence the time of flowering and suitability of flowers for hybridization. Artificial hybridization is typically successful between about 26° C. and about 32° C.

Self-pollination can occur naturally in sweet basil with no manipulation of the flowers. In some examples, the crossing of two sweet basil plants is accomplished using artificial hybridization. In artificial hybridization, the flower used as a female in a cross is manually cross pollinated prior to maturation of pollen from the flower, thereby preventing self-fertilization, or alternatively, the male parts of the flower are emasculated using known methods. Exemplary methods for emasculating the male parts of a sweet basil flower include physical removal of the male parts, use of a cytoplasmic or genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed, for example with forceps. Immature buds, such as those hidden under the stipules at the leaf axil, are removed. The calyx is removed, for example by grasping a sepal with the forceps, pulling it down and around the flower, and repeating the procedure until the five sepals are removed. The exposed corolla is removed, for example by grasping it just above the calyx scar, then lifting and wiggling the forceps simultaneously. The ring of anthers is visible after the corolla is removed, unless the anthers were removed with the petals. Cross-pollination can then be performed using, for example, petri dishes or envelopes in which male flowers have been collected. Desiccators containing calcium chloride crystals are used in some environments to dry male flowers to obtain adequate pollen shed.

Emasculation is not necessary to prevent self-pollination (Walker et al. 1979. *Crop Sci.* 19:285-286). When emasculation is not used, the anthers near the stigma can be removed to make the stigma visible for pollination. The female flower is usually hand-pollinated immediately after it is prepared; although a delay of several hours does not reduce seed set. Pollen shed typically begins in the morning and can end when temperatures are above about 30° C. Pollen shed can also begin later and continue throughout much of the day with more moderate temperatures.

Pollen is available from a flower with a recently opened corolla, but the degree of corolla opening associated with pollen shed can vary during the day. In many environments, collection and use of male flowers immediately without storage can be conducted. In the southern U.S. and other humid climates, pollen shed occurs in the morning when female flowers are more immature and difficult to manipulate than in the afternoon, and the flowers can be damp from heavy dew. In those circumstances, male flowers are collected into envelopes or petri dishes in the morning, and the open container is typically placed in a desiccator for about 4 hours at a temperature of about 25° C. The desiccator can be taken to the field in the afternoon and kept in the shade to prevent excessive temperatures from developing within it. Pollen viability can be maintained in flowers for up to about 2 days when stored at about 5° C. In a desiccator at about 3° C., flowers can be stored successfully for several weeks; however, varieties can differ in the percentage of pollen that germinates after long-term storage.

Either with or without emasculation of the female flower, hand pollination can be carried out by removing the stamens and pistil from a flower of the male parent and gently brushing the anthers against the stigma of the female flower. Access to the stamens can be achieved by removing the front sepal and keel petals, or piercing the keel with closed forceps and allowing them to open to push the petals away. Brushing the anthers on the stigma causes them to rupture, and high percentages of successful crosses are typically obtained when pollen is clearly visible on the stigma. Pollen shed can be checked by tapping the anthers before brushing the stigma. Several male flowers can be used to obtain suitable pollen shed when conditions are unfavorable, or the same male can be used to pollinate several flowers with good pollen shed.

When male flowers are not collected and dried in a desiccator, the parents of a cross can be planted adjacent to each other. Plants are typically grown in rows about 65 cm to about 100 cm apart. Yield of self-pollinated seed from an individual plant can range from a few seeds to more than about 1,000 as a function of plant density. A density of about 30 plants/m of row can be used when about 30 or fewer seeds per plant is adequate, about 10 plants/m can be used to obtain about 100 seeds/plant, and about 3 plants/m usually results in a high seed production per plant. Densities of about 12 plants/m or less are commonly used for artificial hybridization.

Multiple planting dates about 7 days to about 14 days apart can typically be used to match parents of different flowering dates. When differences in flowering dates are extreme between parents, flowering of the later parent can be hastened by creating an artificially short day. Alternatively, flowering of the earlier parent can be delayed by use of artificially long days or delayed planting. For example, crosses with genotypes adapted to the southern U.S. are made in northern U.S. locations by covering the late genotype with a box, large can, or similar container to create an artificially short photoperiod of about 12 hours for about 15 days beginning when there are three nodes with trifoliate leaves on the main stem. Plants induced to flower early tend to have flowers that self-pollinate when they are small and can be difficult to prepare for hybridization. Grafting can be used to hasten the flowering of late flowering genotypes.

Sweet Basil Plants Having One or More Desired Heritable Traits

The disclosure provides plants of the new sweet basil varieties 'Thunderstruck', 'Passion', 'Obsession', 'Rutgers Devotion DMR', '26_24_33', '50_03_05', '50_03_34', and '42_21_02', modified to include one or more desired heritable traits. In some examples, such plants can be developed using backcrossing or genetic engineering (for example by introducing one or more transgenes into a disclosed new sweet basil variety 'Thunderstruck', 'Passion', 'Obsession', 'Rutgers Devotion DMR', '26_24_33', '50_03_05', '50_03_34', and '42_21_02', wherein the transgenes encode one or more desired traits), wherein essentially all of the desired morphological and physiological characteristics of a new disclosed sweet basil variety are recovered (such as BDM resistance/tolerance) in addition to a genetic locus transferred into the plant via the backcrossing technique. Plants developed using such methods can be referred to as a single locus converted plant.

In one example, the method of introducing one or more desired traits into one or more of the disclosed sweet basil varieties ('Thunderstruck', 'Passion', 'Obsession', 'Rutgers Devotion DMR', '26_24_33', '50_03_05', '50_03_34', and '42_21_02') includes (a) crossing a first plant of sweet basil variety 'Thunderstruck', 'Passion', 'Obsession', 'Rutgers Devotion DMR', '26_24_33', '50_03_05', '50_03_34', and '42_21_02' with a second sweet basil plant having one or more desired traits to produce $F_1$ progeny plants; (b) selecting $F_1$ progeny plants that have the one or more desired traits to produce selected $F_1$ progeny plants; (c) crossing the selected progeny plants with at least a first plant of the new variety to produce backcross progeny plants; (d) selecting backcross progeny plants that have the one or more desired traits and physiological and morphological characteristics of a new sweet basil variety to produce selected backcross progeny plants; and (e) repeating steps (c) and (d) one or more times in succession to produce selected second or higher backcross progeny plants that have the one or more desired traits and the physiological and morphological characteristics of a new sweet basil variety 'Thunderstruck', 'Passion', 'Obsession', 'Rutgers Devotion DMR', '26_24_33', '50_03_05', '50_03_34', or '42_21_02' when grown in the same environmental conditions.

Backcrossing methods can be used to improve or introduce a characteristic into a sweet basil variety 'Thunderstruck', 'Passion', 'Obsession', 'Rutgers Devotion DMR', '26_24_33', '50_03_05', '50_03_34', or '42_21_02'. The parental sweet basil plant, which contributes the locus for the desired characteristic, is termed the "nonrecurring" or "donor" parent. This terminology refers to the fact that the nonrecurring parent is used one time in the backcross protocol and therefore does not recur. The parental sweet basil plant to which the locus or loci from the nonrecurring parent are transferred is known as the recurrent parent as it is used for several rounds in the backcrossing protocol (Poehlman and Sleper. 1995. "Breeding Field Crops" Ames, Iowa: Iowa State University Press; Sprague and Dudley, eds. 1988. Corn and Improvement, 3rd edition). In a typical backcross protocol, the original variety of interest (recurrent parent, e.g., the 'Thunderstruck', 'Passion', 'Obsession', 'Rutgers Devotion DMR', '26_24_33', '50_03_05', '50_03_34', or '42_21_02' variety disclosed herein) is crossed to a second variety (nonrecurring parent) that carries the single locus of interest (such as a desirable trait) to be transferred. The resulting progeny from this cross are then crossed again to the recurrent parent and the process is repeated until a Sweet basil plant is obtained wherein essentially all of the desired morphological and physiological characteristics of the recurrent parent (e.g., the 'Thunderstruck', 'Passion', 'Obsession', 'Rutgers Devotion DMR', '26_24_33', '50_03_05', '50_03_34', or '42_21_02' variety disclosed herein) are recovered (such as increased tolerance and/or resistance to downy mildew) in the converted plant, in addition to the single transferred locus from the nonrecurring parent.

A backcross protocol alters or substitutes a single trait or characteristic in the original variety, such as a 'Thunderstruck', 'Passion', 'Obsession', 'Rutgers Devotion DMR', '26_24_33', '50_03_05', '50_03_34', or '42_21_02' sweet basil variety disclosed herein. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent can depend on the purpose of the backcross; for example, a major purpose is to add a commercially desirable, agronomically important trait to the plant. The exact backcrossing protocol can depend on the characteristic or trait being altered to determine an appropriate testing protocol. Although backcrossing methods are simplified when the characteristic being transferred is a dominant allele, a recessive allele can also be transferred. In this instance, it can be useful to introduce a test of the progeny to determine if the desired characteristic has been successfully transferred.

In a backcross where the desired characteristic being transferred to the recurrent parent is controlled by a major gene which can be readily evaluated during the backcrossing, it is common to conduct enough backcrosses to avoid testing individual progeny for specific traits such as yield in extensive replicated tests. In general, four or more backcrosses are used when there is no evaluation of the progeny for specific traits, such as yield. As in this example, lines with the phenotype of the recurrent parent can be composited without the usual replicated tests for traits such as yield, in the individual lines.

Sweet basil varieties can also be developed from more than two parents, for example using modified backcrossing, which uses different recurrent parents during the backcrossing. Modified backcrossing can be used to replace the original recurrent parent with a variety having certain more desirable characteristics, or multiple parents can be used to obtain different desirable characteristics from each.

Many single locus traits are known that are not regularly selected for in the development of a new inbred but that can be improved by backcrossing techniques. Single locus traits can be, but are not necessarily, transgenic. Examples of these traits include, but are not limited to, male sterility, herbicide resistance, abiotic stress tolerance (such as tolerance or resistance to drought, heat, cold, low or high soil pH level, and/or salt), resistance to bacterial, fungal, or viral disease (such as BDM), insect resistance, restoration of male fertility, enhanced nutritional quality, modified phosphorus characteristics, modified antioxidant characteristics, yield stability, and yield enhancement. These comprise genes generally inherited through the nucleus. Thus plants of a 'Thunderstruck', 'Passion', 'Obsession', 'Rutgers Devotion DMR', '26_24_33', '50_03_05', '50_03_34', or '42_21_02' sweet basil variety disclosed herein, or progeny thereof, which include a single locus conversion (such as one that confers a desired trait, such as to BDM resistance/tolerance).

Direct selection can be applied where the single locus acts as a dominant trait. An example of a dominant trait is the herbicide resistance trait (such as glyphosate resistance). For the selection process, the progeny of the initial cross are sprayed with a herbicide (such as RoundUp® herbicide) prior to the backcrossing. The spraying eliminates any plants which do not have the desired herbicide resistance characteristic; only those plants which have the herbicide resistance gene are used in the subsequent backcross. This process is then repeated for all additional backcross generations.

Selection of sweet basil plants for breeding may not be dependent on the phenotype of a plant and instead can be based on genetic investigations. For example, a suitable genetic marker can be used which is genetically-linked to a desired trait. One of these markers can therefore be used to identify the presence or absence of a trait in the offspring of a particular cross, and hence can be used in selection of progeny for continued breeding. This technique is referred to as marker assisted selection. Any other type of genetic marker or other assay which is able to identify the relative presence or absence of a trait of interest in a plant can also be useful for breeding. Procedures for marker assisted selection applicable to plant breeding are well known. Such methods can be useful in the case of recessive traits and variable phenotypes, or where conventional assays are more expensive, time consuming, or otherwise disadvantageous. Types of genetic markers which can be used, but are not limited to, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, which is incorporated herein by reference in its entirety), and Single Nucleotide Polymorphisms (SNPs).

Qualitative characteristics can also be useful as phenotype-based genetic markers in Sweet basil; however, some or many may not differ among varieties commonly used as parents. Exemplary genetic markers include flower color, differences in maturity, height, and pest resistance.

Useful or desirable traits can be introduced by backcrossing, as well as directly into a plant by genetic transformation methods. Genetic transformation can therefore be used to insert a selected transgene into the 'Thunderstruck', 'Passion', 'Obsession', 'Rutgers Devotion DMR', '26_24_33', '50_03_05', '50_03_34', or '42_21_02' sweet basil variety disclosed herein or progeny thereof, or can, alternatively, be used for the preparation of transgenes which can be introduced by backcrossing. Thus, the disclosure provides methods of producing a plant of the 'Thunderstruck', 'Passion', 'Obsession', 'Rutgers Devotion DMR', '26_24_33', '50_03_05', '50_03_34', or '42_21_02' sweet basil variety disclosed herein, or progeny thereof, that includes one or more added desired traits, for example that include introducing a transgene(s) conferring the one or more desired traits into the 'Thunderstruck', 'Passion', 'Obsession', 'Rutgers Devotion DMR', '26_24_33', '50_03_05', '50_03_34', or '42_21_02' sweet basil variety disclosed herein or progeny thereof (for example by transformation with a transgene that confers upon the sweet basil plant the desired trait), thereby producing a plant of the 'Thunderstruck', 'Passion', 'Obsession', 'Rutgers Devotion DMR', '26_24_33', '50_03_05', '50_03_34', or '42_21_02' sweet basil variety disclosed herein or progeny thereof that includes the one or more added desired traits.

Methods for the transformation of plants, including sweet basil, are known. Methods for introducing a desired nucleic acid molecule (e.g., transgene), such as DNA, RNA, or inhibitory RNAs, which can be employed for the genetic transformation of sweet basil include, but are not limited to, electroporation, microprojectile bombardment, *Agrobacterium*-mediated transformation and direct DNA uptake by protoplasts.

To effect transformation by electroporation, friable tissues, such as a suspension culture of cells or embryogenic callus, can be used. Alternatively, immature embryos or other organized tissue can be transformed directly. In this technique, the cell walls of target cells can be partially degraded by exposing them to pectin-degrading enzymes (pectolyases) or mechanically wound tissues in a controlled manner. Protoplasts can also be employed for electroporation transformation of plants (Bates. 1994. *Mol. Biotechnol.* 2(2):135-145; Lazzeri. 1995. *Methods Mol. Biol.* 49:95-106).

In microprojectile bombardment, particles (such as those comprised of tungsten, platinum, or gold) are coated with nucleic acids and delivered into cells by a propelling force. For the bombardment, cells in suspension are concentrated on filters or solid culture medium. Alternatively, immature embryos or other target cells can be arranged on solid culture medium. The cells to be bombarded are positioned at an appropriate distance below the macroprojectile stopping plate. An exemplary method for delivering DNA into plant cells by acceleration is the Biolistics Particle Delivery System, which can be used to propel particles coated with DNA or cells through a screen, such as a stainless steel or Nytex screen, onto a surface covered with target Sweet basil cells. The screen disperses the particles so that they are not delivered to the recipient cells in large aggregates. A screen intervening between the projectile apparatus and the cells to be bombarded can reduce the size of projectiles aggregate and contribute to a higher frequency of transformation by reducing the damage inflicted on the recipient cells by projectiles that are too large.

*Agrobacterium*-mediated transfer is a method for introducing gene loci into plant cells. DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations (Klee et al. 1985. *Bio. Tech.* 3(7):637-342). Moreover, vectors for *Agrobacterium*-mediated gene transfer have improved the arrangement of genes and restriction sites in the vectors to facilitate the construction of vectors capable of expressing various polypeptide coding genes. Such vectors have convenient multi-linker regions flanked by a promoter and a polyadenylation site for direct expression of inserted polypeptide coding genes. Additionally, *Agrobacterium* containing both armed and disarmed Ti genes can be used for transformation. The use of *Agrobacterium*-mediated plant integrating vectors to introduce DNA into plant cells is known (e.g., Fraley et al. 1985. *Bio. Tech.*

3(7):629-635; U.S. Pat. No. 5,563,055). Briefly, plant tissue (often leaves) is cut into small pieces, e.g. 10 mm×10 mm, and soaked for 10 minutes in a fluid containing suspended *Agrobacterium*. Some cells along the cut will be transformed by the bacterium, which inserts its DNA into the cell, which is placed on selectable rooting and shooting media, allowing the plants to regrow. Some plants can be transformed just by dipping the flowers into suspension of *Agrobacterium* and then planting the seeds in a selective medium. Sweet basil has been transformed using *Agrobacterium* (Dechamps and Simon. 2002. *Plant Cell Reports* 21:359-364).

Transformation of plant protoplasts can also be achieved using methods based on calcium phosphate precipitation, polyethylene glycol treatment, electroporation, and combinations of these treatments (e.g., Potrykus et al. 1985. *Mol. Gen. Genet.* 199(2):169-177; Omirulleh et al. 1993. *Plant Mol. Biol.* 21(3):415-428; Fromm et al. 1986. *Nature.* 319 (6056):791-739; Uchimiya et al. 1986. *Mol. Gen. Genet.* 204(2):207-207; Marcotte et al. 1988. *Nature* 335(6189): 454-457).

In one example, such methods can also be used to introduce transgenes for the production of proteins in transgenic sweet basil cells. The resulting produced protein can be harvested from the transgenic sweet basil. The transgene can be harvested from the transgenic plants that are originated or are descended from the new sweet basil variety disclosed herein, a seed of such a sweet basil or a hybrid progeny of such a sweet basil.

Numerous different genes are known and can be introduced into the 'Thunderstruck', 'Passion', 'Obsession', 'Rutgers Devotion DMR', '26_24_33', '50_03_05', '50_03_34', or '42_21_02' sweet basil variety disclosed herein, or progeny thereof. Non-limiting examples of particular genes and corresponding phenotypes that can be chosen for introduction into a sweet basil plant are provided herein Herbicide Resistance A herbicide resistance gene can be used with the methods and plants provided herein. In particular examples, a herbicide resistance gene confers tolerance to an herbicide comprising glyphosate, sulfonylurea, imidazalinone, dicamba, glufosinate, phenoxy proprionic acid, cyclohexone, triazine, benzonitrile, broxynil, L-phosphinothricin, cyclohexanedione, chlorophenoxy acetic acid, or combinations thereof.

In one example the herbicide resistance gene is a gene that confers resistance to an herbicide that inhibits the growing point or meristem, such as an imidazalinone or a sulfonylurea. Exemplary genes in this category code for mutant ALS and AHAS enzyme as described, for example, by Lee et al. (1988. *Embryo J.* 7:1241-8) and Miki et al. (1990. *Theoret. Appl. Genet.* 80:449-458).

Resistance genes for glyphosate (resistance conferred by mutant 5-enolpyruvl-3 phosphikimate synthase (EPSP) and aroA genes, respectively) and other phosphono compounds such as glufosinate (phosphinothricin acetyl transferase (PAT) and *Streptomyces hygroscopicus* phosphinothricin-acetyl transferase (bar) genes) can be used (e.g., see U.S. Pat. No. 4,940,835). Examples of specific EPSPS transformation events conferring glyphosate resistance are described, for example, in U.S. Pat. No. 6,040,497.

DNA molecules encoding a mutant aroA gene are known (e.g., ATCC accession number 39256 and U.S. Pat. No. 4,769,061), as are sequences for glutamine synthetase genes, which confer resistance to herbicides such as L-phosphinothricin (e.g., U.S. Pat. No. 4,975,374), phosphinothricin-acetyltransferase (e.g., U.S. Pat. No. 5,879,903). DeGreef et al. (1989. *Bio/Technology* 61-64) describe the production of transgenic plants that express chimeric bar genes coding for phosphinothricin acetyl transferase activity. Exemplary genes conferring resistance to phenoxy propionic acids and cyclohexones, such as sethoxydim and haloxyfop are the Acct-S1, Accl-S2 and Acct-S3 genes described by Marshall et al. (1992. *Theor Appl Genet.* 83:435-442).

Exemplary genes conferring resistance to an herbicide that inhibits photosynthesis include triazine (psbA and gs+genes) and benzonitrile (nitrilase gene) (see Przibilla et al., 1991. *Plant Cell.* 3:169-174). Nucleotide sequences for nitrilase genes are disclosed in U.S. Pat. No. 4,810,648, and DNA molecules containing these genes are available under ATCC Accession Nos. 53435, 67441, and 67442. Cloning and expression of DNA coding for a glutathione S-transferase is described by Hayes et al. (1992. *Biochem. J.* 285:173).

U.S. Patent Publication No: 20030135879 describes dicamba monooxygenase (DMO) from *Pseuodmonas maltophilia*, which is involved in the conversion of a herbicidal form of the herbicide dicamba to a non-toxic 3,6-dichlorosalicylic acid and thus can be used for producing plants tolerant to this herbicide.

The metabolism of chlorophenoxyacetic acids, such as, for example 2,4-D herbicide, is well known. Genes or plasmids that contribute to the metabolism of such compounds are described, for example, by Muller et al. (2006. *Appl. Environ. Microbiol.* 72(7):4853-4861), Don and Pemberton (1981. *J Bacteriol* 145(2):681-686), Don et al. (1985. *J Bacteriol* 161(1):85-90) and Evans et al. (1971. *Biochem J* 122(4):543-551).

Disease Resistance

Plant defenses are often activated by specific interaction between the product of a disease resistance gene (R) in the plant and the product of a corresponding avirulence (Avr) gene in the pathogen. A plant, such as the 'Thunderstruck', 'Passion', 'Obsession', 'Rutgers Devotion DMR', '26_24_33', '50_03_05', '50_03_34', or '42_21_02' sweet basil variety disclosed herein or progeny thereof, can be transformed with cloned resistance gene to engineer plants that are resistant to specific pathogen strains. See, for example Jones et al. (1994. *Science* 266:789) (tomato Cf-9 gene for resistance to *Cladosporium falvum*); Martin et al. (1993. *Science* 262(5138):1432-1436) (tomato Pto gene for resistance to *Pseudomonas syringae* pv.); and Mindrinos et al. (1994. *Cell* 78:1089-1099) (*Arabidopsis* RSP2 gene for resistance to *Pseudomonas syringae*).

A viral-invasive protein or a complex toxin derived therefrom can also be used for viral disease resistance. For example, the accumulation of viral coat proteins in transformed plant cells imparts resistance to viral infection and/or disease development effected by the virus from which the coat protein gene is derived, as well as by related viruses. See Beachy et al. (1990. *Annu Rev Phytopathol* 28:451-474). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

A virus-specific antibody can also be used. See, for example, Tavladoraki et al. (1993. *Nature* 366:469-472), which shows that transgenic plants expressing recombinant antibody genes are protected from virus attack.

Logemann et al. (1992. *Bio/Technology* 10:305-308) disclose transgenic plants expressing a barley ribosome-inactivating gene have an increased resistance to fungal disease. Insect Resistance One example of an insect resistance gene includes a *Bacillus thuringiensis* (Bt) protein, a derivative thereof or a synthetic polypeptide modeled thereon (e.g., see Geiser et al., 1986. *Gene* 48:109, discloses a Bt Δendotoxin gene). Moreover, DNA molecules encoding Δ-endotoxin genes can be obtained from the ATCC (Manassas, Va.), for example under ATCC Accession Nos. 40098, 67136, 31995 and 31998. Another example is a lectin. See, for example, Van Damme et al. (1994. *Plant Mol Biol* 24(5):825-830), which discloses several *Clivia miniata* mannose-binding lectin genes. A vitamin-binding protein can also be used, such as avidin. See WIPO Publication No. WO 1994/000992, which teaches the use of avidin and avidin homologues as larvicides against insect pests.

In one example the insect resistance gene is an enzyme inhibitor, for example, a protease, proteinase inhibitor, or an a-amylase inhibitor. See, for example, Abe et al. (1987. *J. Biol. Chem.* 262:16793-7; discloses a rice cysteine proteinase inhibitor), Genbank Accession Nos. Z99173.1 and DQ009797.1 which disclose proteinase inhibitor coding sequences, and Sumitani et al. (1993. *Plant Mol. Biol.* 21:985; discloses *Streptomyces nitrosporeus* α-amylase inhibitor). An insect-specific hormone or pheromone can also be used. See, for example, Hammock et al. (1990. *Nature* 344:458-461; discloses juvenile hormone esterase, an inactivator of juvenile hormone).

Still other examples include an insect-specific antibody or an immunotoxin derived therefrom and a developmental-arrestive protein. See Taylor et al. (1994. Seventh Intl. Symposium on Molecular Plant-Microbe Interactions (Edinburgh Scotland), Abstract #497), who described enzymatic inactivation in transgenic tobacco via production of single-chain antibody fragments.

Male Sterility

Genetic male sterility can increase the efficiency with which hybrids are made, in that it can eliminate the need to physically emasculate the Sweet basil plant used as a female in a given cross (Brim and Stuber. 1973. *Crop Sci.* 13:528-530). Herbicide-inducible male sterility systems are known (e.g., U.S. Pat. No. 6,762,344).

Where use of male-sterility systems is desired, it can be beneficial to also utilize one or more male-fertility restorer genes. For example, where cytoplasmic male sterility (CMS) is used, hybrid seed production involves three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Such hybrids are useful where the vegetative tissue of the Sweet basil plant is utilized. However, in many cases, the seeds are considered to be a valuable portion of the crop, thus, it is desirable to restore the fertility of the hybrids in these crops. Therefore, the disclosure provides plants of the 'Thunderstruck', 'Passion', 'Obsession', 'Rutgers Devotion DMR', '26_24_33', '50_03_05', '50_03_34', or '42_21_02' sweet basil variety disclosed herein comprising a genetic locus capable of restoring male fertility in an otherwise male-sterile plant. Examples of male-sterility genes and corresponding restorers which can be employed are well known (see, e.g., U.S. Pat. No. 5,530,191 and U.S. Pat. No. 5,684,242).

Tissue Cultures and In Vitro Regeneration of Sweet Basil Plants

Tissue cultures of one or more of the 'Thunderstruck', 'Passion', 'Obsession', 'Rutgers Devotion DMR', '26_24_33', '50_03_05', '50_03_34', or '42_21_02' sweet basil variety are provided. A tissue culture includes isolated cells of the same or a different type or a collection of such cells organized into parts of a plant. Exemplary types of tissue cultures include protoplasts, calli and plant cells that are intact in plants or parts of plants, such as embryos, pollen, flowers, leaves, roots, root tips, anthers, meristematic cells, pistil, seed, petiole, stein, ovule, cotyledon, hypocotyl, shoot or stem, and the like. In a particular example, the tissue culture includes embryos, protoplasts, meristematic cells, pollen, leaves or anthers of the 'Thunderstruck', 'Passion', 'Obsession', 'Rutgers Devotion DMR', '26_24_33', '50_03_05', '50_03_34', and/or '42_21_02' sweet basil variety disclosed herein. Also provided are sweet basil plants regenerated from such tissue cultures, wherein the regenerated sweet basil plant expresses the physiological and morphological characteristics of a new sweet basil variety disclosed herein.

Methods for preparing tissue cultures of regenerable sweet basil cells and regenerating sweet basil plants therefrom, are known, such as those disclosed in U.S. Pat. Nos. 4,992,375; 5,015,580; 5,024,944, and 5,416,011. Tissue culture provides the capability to regenerate fertile plants. This can allow, for example, transformation of the tissue culture cells followed by regeneration of transgenic plants. For transformation to be efficient and successful, DNA can be introduced into cells that give rise to plants or germ-line tissue.

Sweet basil plants can be regenerated using shoot morphogenesis or somatic embryogenesis. Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos, while lines that produce large numbers of embryos during an "induction" step may not give rise to rapidly-growing proliferative cultures. In addition to line-specific responses, proliferative cultures can be observed with both shoot morphogenesis and somatic embryogenesis. Proliferation allows a single, transformed cell to multiply to the point that it can contribute to germ-line tissue.

Shoot morphogenesis is a system whereby shoots are obtained de novo from cotyledonary nodes of Sweet basil seedlings (Wright et al., 1986. *Plant Cell Reports* 5:150-154). The shoot meristems form subepidermally and morphogenic tissue can proliferate on a medium containing benzyl adenine (BA). This system can be used for transformation if the subepidermal, multicellular origin of the shoots is recognized and proliferative cultures are utilized. Tissue that can give rise to new shoots are targeted and proliferated within the meristematic tissue to lessen problems associated with chimerism.

Somatic embryogenesis in sweet basil is a system in which embryogenic tissue is obtained from the zygotic embryo axis (Christianson et al., 1983. *Science* 222:632-634). The embryogenic cultures are proliferative and the proliferative embryos are of apical or surface origin with a small number of cells contributing to embryo formation. The origin of primary embryos (the first embryos derived from the initial explant) is dependent on the explant tissue and the auxin levels in the induction medium (Hartweck et al., 1988. *In Vitro Cell. Develop. Bio.* 24:821-828). With proliferative embryonic cultures, single cells or small groups of surface cells of the "older" somatic embryos form the "newer" embryos.

Embryogenic cultures can also be used for regeneration, including regeneration of transgenic plants.

Methods of Making Extracts from Sweet Basil

Extracts can be generated from the 'Thunderstruck', 'Passion', 'Obsession', 'Rutgers Devotion DMR', '26_24_33', '50_03_05', '50_03_34', and/or '42_21_02' sweet basil variety or progeny thereof. Such extracts can be used in aroma and flavoring and medicinal or health oriented plant based extracts. In some examples, the extract includes genetic material from the 'Thunderstruck', 'Passion', 'Obsession', 'Rutgers Devotion DMR', '26_24_33', '50_03_05', '50_03_34', and/or '42_21_02' sweet basil variety, such as a cell from the 'Thunderstruck', 'Passion', 'Obsession', 'Rutgers Devotion DMR', '26_24_33', '50_03_05', '50_03_34', and/or '42_21_02' sweet basil variety.

In one example, plants of the 'Thunderstruck', 'Passion', 'Obsession', 'Rutgers Devotion DMR', '26_24_33', '50_03_05', '50_03_34', and/or '42_21_02' sweet basil variety, or any above-ground part of the plant, are harvested, for example, after at least 20 days, at least 30 days, at least 45 days, at least 60 days, at least 70 days, at least 90 days, at least 100 days, or at least 120 days of growth (such as after 45 to 100 days, 60 to 100 days, or 50 to 90 days, such as after 60 days or 90 days of growth). The plant can be dried, for example by leaving it in the field to partially dry, or brought indoors to be flash frozen, frozen, boiled, heated, or dried, for example at 37° C. (e.g., by air drying, microwaving, lyophilization, or combinations thereof, such as by using a Powell walk-in forced air dryer) or other drying system until no further moisture loss is noted under the temperature and pressure and relative humidity of the drying system. The leaves and flowers of the plant can be separated from the stems, for example manually or by machine. Essential oils can be extracted from the dried leaves and flowers using steam or hydro-distillation or hot water. In some examples, solvent extraction and super critical fluids are used.

The sweet basil from which an extract is generated can be field-grown, greenhouse grown or grown in pots, sacs and containers, and cut at any height above the soil, and the plant distilled fresh or partially dried to obtain the aromatic essential oil. Sweet basil plants are typically cut once per growing season, but the 'Thunderstruck', 'Passion', 'Obsession', 'Rutgers Devotion DMR', '26_24_33', '50_03_05', '50_03_34', and '42_21_02' sweet basil varieties can be harvested (or cut) once or twice or more per growing season, provided it is grown with ample water, nutrients and under environmental conditions that result in plant growth and development. Once harvested, the plant can be distilled immediately, allowed to be partially dried in full sun, partial sun in the field and then placed into a container for steam or hydro-distillation or allowed to further dried and processed at future time. Other processes can also be used, including but not limited to, solvent extraction. For an extract or dry product, the sweet basil may be sun dried, dried in shade, with or without artificial heat introduced by different sources, and then allowed to dry before extraction.

Products Containing Sweet Basil

The disclosure provides products obtained from one or more of the new varieties ('Thunderstruck', 'Passion', 'Obsession', 'Rutgers Devotion DMR', '26_24_33', '50_03_05', '50_03_34', and '42_21_02') disclosed herein, or progeny thereof. Exemplary products include a biomass or part thereof, such as an extract, oil, protein isolate, protein concentrate, oil extract, or leaves. For example a dried biomass and/or leaves of one or more of the new varieties ('Thunderstruck', 'Passion', 'Obsession', 'Rutgers Devotion DMR', '26_24_33', '50_03_05', '50_03_34', and '42_21_02') or progeny thereof can be used as part of food, beverage, or aroma-based product. In some examples, the product includes at least one cell, DNA, and/or protein of sweet basil variety 'Thunderstruck', 'Passion', 'Obsession', 'Rutgers Devotion DMR', '26_24_33', '50_03_05', '50_03_34', and '42_21_02'.

The disclosure provides containers, such as a glass, paper, or plastic container, which includes leaves of one or more of the new varieties ('Thunderstruck', 'Passion', 'Obsession', 'Rutgers Devotion DMR', '26_24_33', '50_03_05', '50_03_34', and '42_21_02'). The leaves can be dried, frozen, or fresh. In some examples, the container includes leaves (or other parts) from other plants, such as oregano, parsley, marjoram, thyme, rosemary, or non sweet basils, or combinations thereof. In some examples, the container includes garlic, such as dried or fresh garlic.

Provided herein is a dried tea, food and flavor or fragrance product which includes leaves or comes from an oil extract, and/or biomass of one or more of the new varieties ('Thunderstruck', 'Passion', 'Obsession', 'Rutgers Devotion DMR', '26_24_33', '50_03_05', '50_03_34', and '42_21_02') or progeny thereof. Also provided is a liquid tea, produced from leaves, oil extract, and/or biomass of one or more of the new varieties ('Thunderstruck', 'Passion', 'Obsession', 'Rutgers Devotion DMR', '26_24_33', '50_03_05', '50_03_34', and '42_21_02') or progeny thereof.

Provided herein are pet toys or aromatic toys/balls/ornamentals/aromatic wreaths/other personal consumer items, which include leaves, oil extract, and/or biomass of one or more of the new varieties ('Thunderstruck', 'Passion', 'Obsession', 'Rutgers Devotion DMR', '26_24_33', '50_03_05', '50_03_34', and '42_21_02') or progeny thereof.

Oil extracts of one or more of the new varieties ('Thunderstruck', 'Passion', 'Obsession', 'Rutgers Devotion DMR', '26_24_33', '50_03_05', '50_03_34', and '42_21_02') or progeny thereof are provided, and in one example are formulated into a spray.

EXAMPLE 1

Breeding History

Development was initiated in 2013 upon identification of *Peronospora belbahrii* resistant cultivar 'Mrihani', which was self-pollinated for three generations and is subsequently referred to as MRI. The inbred MRI genotype demonstrated significantly reduced BDM severity in 2013 and 2014 field evaluations (Pyne et al., *J. Amer. Soc. Hort. Sci.*, 140:396-403 2015) and in a greenhouse screening method developed by the inventors (Pyne et al., *HortSci* 49:1041-5, 2014). A second genotype, 'SB22', a Rutgers bred and developed aromatic sweet basil was selected as an inbred line because of its high quality and traditional 'large leaf' sweet basil phenotype and with consistent field and greenhouse susceptibility to *P. belbahrii* in addition to observed tolerance to *Fusarium oxysporum* f. sp. *basilicum* (FOB).

MRI and 'SB22' were cross-pollinated in reciprocal to yield multiple $F_1$ generation plants. A single, resistant $F_1$ plant derived from an MRI mother and 'SB22' father was self-pollinated to yield an $F_2$ generation of 300 individuals. $F_2$ selections were made in a 2013 field test at the Rutgers Agricultural Research and Extension Center (RAREC) in Bridgeton, N.J. from which 32 $F_{2:3}$ families were generated through self-pollination. The $F_{2:3}$ families were subsequently field tested for response to *P. belbahrii* constituting a progeny test for the genotype of downy mildew resistant loci. A single $F_{2:3}$ family, RUMS469, demonstrated a leaf shape and habit most closely resembling the original 'SB22' grandparent and demonstrated no susceptible individuals (i.e., no segregation) indicating homozygous genetic resistance.

A single resistant plant was selected for a phenotype most closely resembling 'SB22' within the RUMS469 family, named RUMS469-11. This individual was used as a mother in a cross with inbred line 'SB13', which was anecdotally observed to have DM tolerance and selected for FOB tolerance, high vigor and large leaf. This RUMS469-11× SB22 cross (RU4S lineage) yielded 60 progeny that were evaluated in 2014 at the Everglades Research and Education Center (EREC) in Belle Glade, Fla., a location selected for extraordinarily high and consistent *P. belbahrii* inoculum levels (i.e., disease pressure). Individual plants showed differential response to disease and 20 resistant plants were selected based on commercial leaf shape, aroma, flavor, flowering time and habit. All progeny resembled commercial 'large leaf' sweet basil phenotypes yet maintained distinct differences in curvature, length, width, margin serration and texture.

Figure 3:
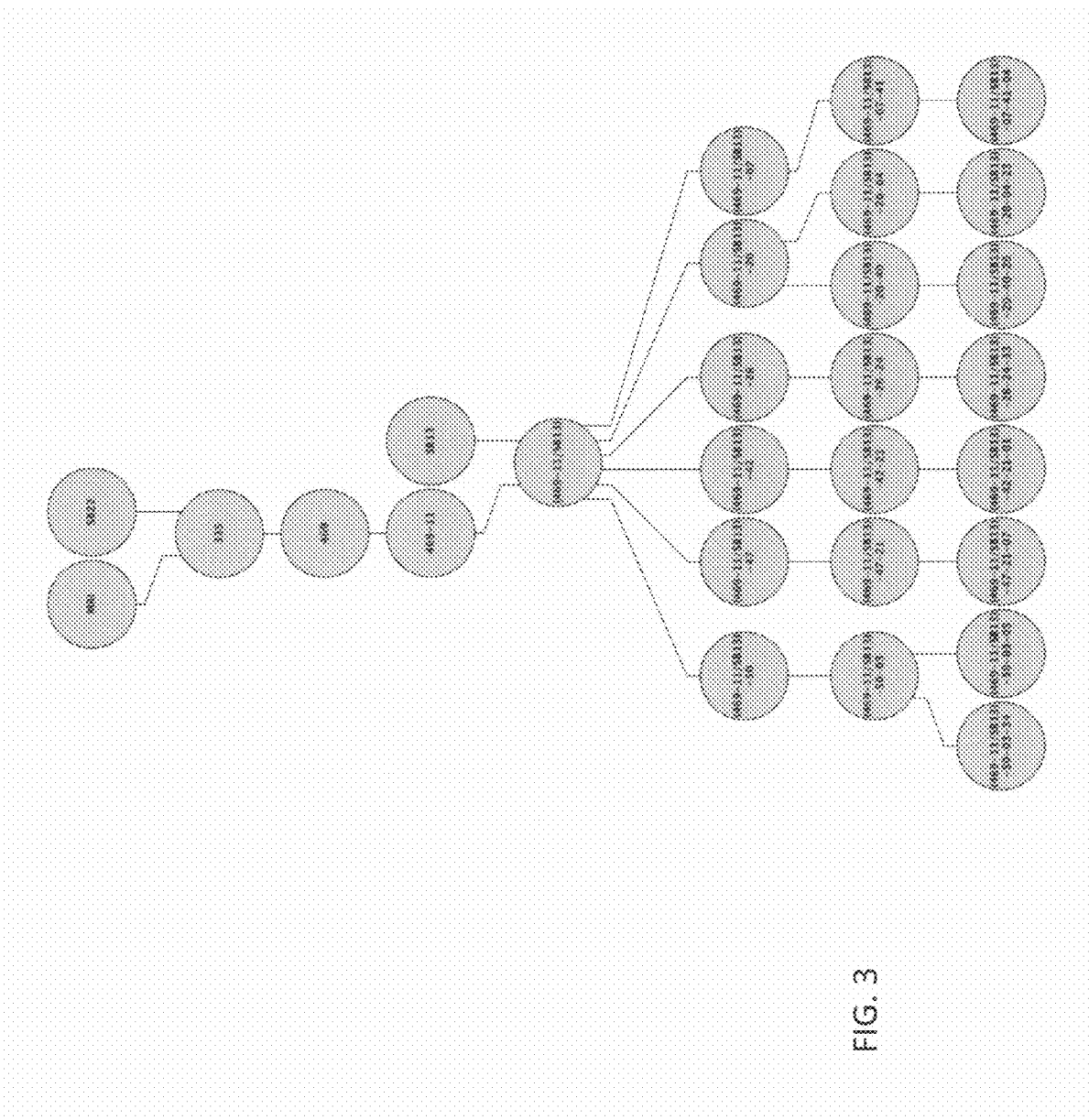
FIG. 3. Pedigree of the new sweet basil varieties. Circles indicate individual plant selections. Demonstrates the pedigree breeding strategy adopted and resulting in the inbred lines shown in the lower most tier of the chart. Circle represent individuals. Lines connecting two circles represent direct descent. A single line connecting two circles indicates a self-pollinated generation, whereas one circle connected to two circles indicates a cross-pollinated generation in which the mother is on the right and father on left. Lowest circles represent 11 completed breeding lines.

Ten individuals were selected for varying leaf shapes in order to potentially serve different markets in need of resistant material. Each RU4S individual was subsequently subjected to two rounds of self-pollination with selection for resistance to ensure homozygous resistant loci as well as phenotypic homogeneity. A final qualitative evaluation for seedling uniformity (where phenotypic differences among individuals are most pronounced) was made in Rutgers Research Greenhouses followed by single plant selection and within homogenous lines for another generation of self-pollination. Eight stable (homogeneous) RU4S lines varying in leaf shape and ranging from full-to-quarter siblings were generated in the form of seed propagules. The genealogy of the new cultivars 'Thunderstruck', 'Passion', 'Obsession', 'Rutgers Devotion DMR', '26_24_33', '50_03_05', '50_03_34', and '42_21_02' is provided in Table 2. A pedigree of the new varieties is provided in FIG. 3.

Table 2: Genealogy of the New Sweet Basil Cultivars

2012 Commercial variety 'Mrihani' is subjected to three generations self-pollination by single seed descent followed by downy mildew resistance confirmation in greenhouse screening. The resulting inbred line, MRI, was hybridized with elite sweet basil inbred line 'SB22'. Reciprocal F1 progeny were generated and the MRI (female)×SB22 (male) F1 self-pollinated to generate an F2 family.

2013 An $F_2$ family of 300 individuals was evaluated for response to downy mildew at the Rutgers Agricultural Research and Extension Center (RAREC) in Bridgeton, N.J. A total of 32 selections achieving the highest category of reduced disease severity were selected for self-pollination in isolation.

2014 The 32 $F_{2:3}$ families of approximately 100 individuals each were evaluated for response to downy mildew at the RAREC in Bridgeton, N.J. Selections were made within families achieving the highest category of reduced disease severity among all individuals indicating no homozygosity for major downy mildew resistance locus or loci. The F2:3 individual RUMS469-11 was selected for hybridization with elite sweet basil inbred line 'SB13', which demonstrates downy mildew and Fusarium wilt tolerance. The RUMS469-11 (female)×SB13 (male) cross provided 60 progeny that were evaluated in 2014

2015 Sixty progeny from the RUMS469-11×SB13 cross were evaluated at the Everglades Research and Education Center (EREC) in Belle Glade, Fla., a location selected for high *P. belbahrii* inoculum levels (i.e., disease pressure). Segregation was observed and 20 individuals were selected, achieving the highest category of reduced disease severity. These individuals were selfed to generate full sibling families evaluated for response to downy mildew at the RAREC location. Selections were made with preference to families not segregating for downy mildew resistance. An additional selection criteria was added for commercial 'large leaf' sweet basil phenotypes with specific attention to leaf curvature, length, width, margin serration and texture. Twenty individuals were selected for varying leaf shapes in order to potentially serve different markets in need of resistant material. These individuals were selfed resulting in 20 full-sibling families.

2016 The resulting 20 families were evaluated in progeny rows at the EREC location where families segregating for downy mildew response were culled and a strong selection pressure was applied using criteria that included phenotype (leaf characteristics, flowering time, flavor/aroma) and phenotype homogeneity within families. Ten selections were made among best performing families with distinct, varying leaf shapes in order to potentially serve different markets in need of resistant material. One generation of single seed descent was performed to increase homogeneity among the ten lines 2017 Performance trials were conducted for the ten selected inbred lines. Biomass, flowering time, leaf characteristics, aroma/flavor were evaluated and four lines were selected for immediate commercialization. Test for seedling uniformity resulted in eight unique sweet basil lines ('Thunderstruck', 'Passion', 'Obsession', 'Rutgers Devotion DMR', '26_24_33', '50_03_05', '50_03_34', and '42_21_02') are described herein.

EXAMPLE 2

Physiological and Morphological Characteristics

Figure 4A:
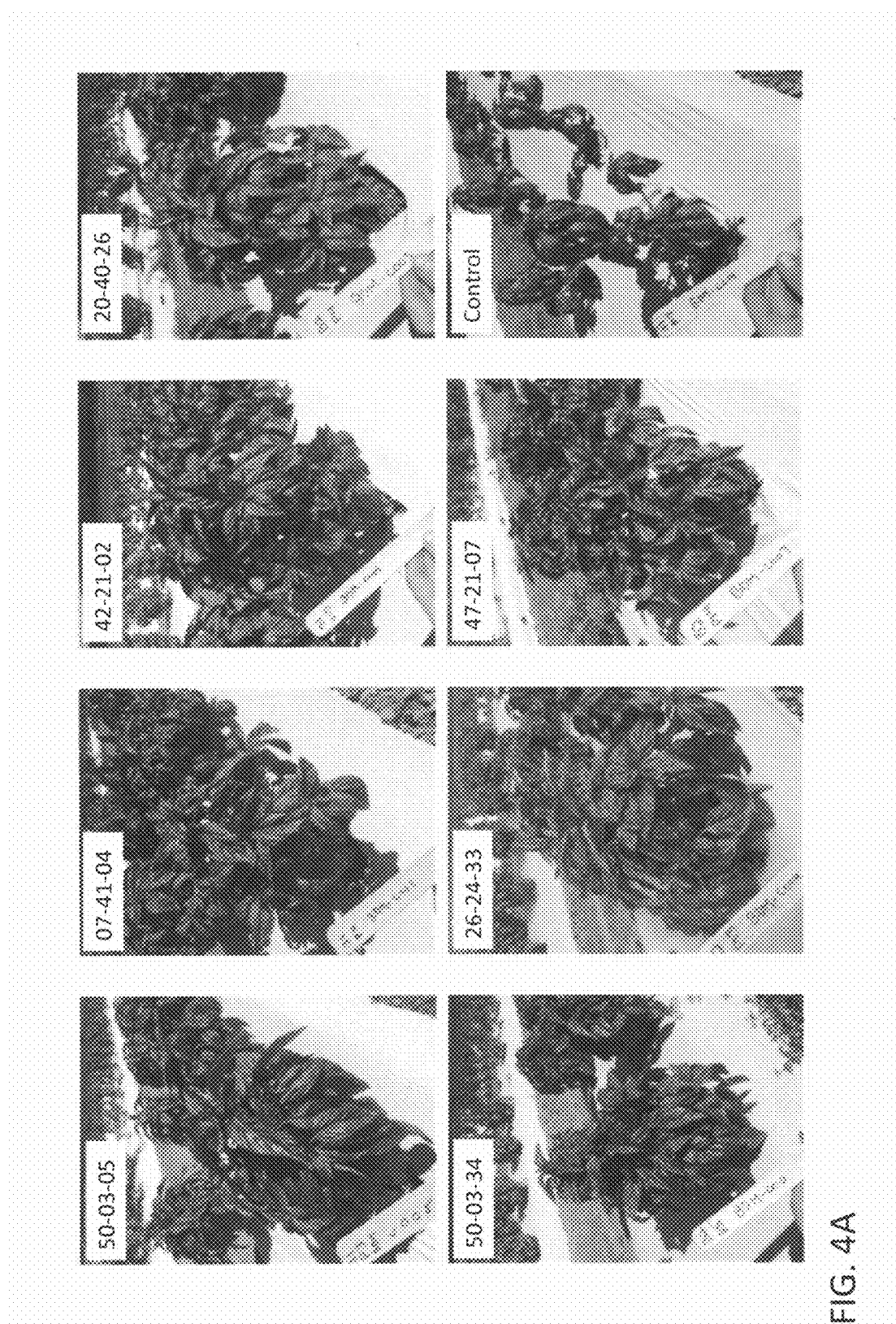
FIG. 4A-4B. Digital images of (A) new sweet basil varieties ('50_03_05', 'Passion', '42_21_02', 'Rutgers Devotion DMR', '50_03_34', '26_24_33', and 'Obsession') compared to commercial control variety 'DiGenova', and (B) variety 'Thunderstruck'. While the new varieties exhibit little or no symptoms from basil downy mildew exposure, the commercial sweet basil control exhibits downy mildew symptoms.
Figure 4B:

The eight new sweet basil cultivars ('Thunderstruck', 'Passion', 'Obsession', 'Rutgers Devotion DMR', '26_24_33', '50_03_05', '50_03_34', and '42_21_02') have not been observed under all possible environmental conditions to date. Accordingly, it is possible that the phenotype may vary somewhat with variations in the environment, such as temperature, light intensity, and day length, without, however, any variance in genotype. Digital images of the new varieties are shown in FIGS. 4A-4B.

Sweet basil plants can be harvested one or more times during each growing season. The eight sweet basil cultivars ('Thunderstruck', 'Passion', 'Obsession', 'Rutgers Devotion DMR', '26_24_33', '50_03_05', '50_03_34', and '42_21_02') can also be kept from flowering by continual pruning.

Biomass

The fresh weight of each variety was calculated by taking the mean fresh weight of each variety at two different locations (Pittstown, N.J. and Bridgeton, N.J.), dividing by the total number of plants harvested from each line and multiplied by 100. The results are shown in Table 3.

Flowering Frequency

The number of inflorescences with at least one whorl of flowers open were counted for each variety at two time points representing first onset (70 days post planting) of flowers and more robust flowering (75 days post planting). The number of plants in flower was divided by the total number of plants per variety to give an estimate of flowering time.

As shown in Table 5, there are differences in flowering time across the cultivars. Late flowering time and resistance to bolting is a desirable agronomic trait especially for basil produced in the field.

TABLE 3

Yield of each of the sweet basil cultivars as determined by biomass (kg) from locations with (NJ) and without (CA) occurrence of downy mildew

| Location | Days after planting | Passion | Thunder-struck | Rutgers Devotion DMR | 26-24-33 | 42-21-02 | Obsession | 50-03-05 | 50-03-34 | Susceptible Control | Commercial Standard |
|---|---|---|---|---|---|---|---|---|---|---|---|
| NJ | 76 | 3.58 | | 3.44 | 3.50 | 3.60 | 2.81 | 2.94 | 2.73 | 1.39 | 2.34 |
| CA | 65 | 2.40 | | 0.80 | 1.80 | 1.55 | | | 0.80 | | 1.00 |
| CA | 91* | 4.22 | | 2.74 | 3.42 | 4.09 | | | 4.22 | | 3.80 |

*This harvest represents the re-growth from the initial harvest 65 days after planting Leaf Serration, Color, Aroma/Flavor Leaf serration was graded on a 0-9 scale with scores of 0 indicating entire leaf margins and increasing scores for increasing degrees of serration. For aroma and flavor, sweet is a descriptor of the traditional sweet basil aroma and flavor. The results are shown in Table 4.

TABLE 4

Morphological characteristics of each sweet basil as score by visual qualitative assessment

| Trait | Possession | Thunder-struck | Rutgers Devotion DMR | 26-24-33 | 42-21-02 | Obsession | 50-03-05 | 50-03-34 | Susceptible Control | Commercial Standard |
|---|---|---|---|---|---|---|---|---|---|---|
| Leaf Color | Shiny green, dark | green | Light green | Dark green | Green, shiny | Dark green | Dark green, shiny | Dark green, shiny | Light green | Green, pale |
| Leaf Serration[1] | 4 | | 4 | 1 | 3 | 3 | 1 | 1 | 0 | 2 |
| Stem Color | Green | Green | Green | Green | Green | Green | Green | Green | Green | Green |
| Flower Color | White | White | White | White | White | White | White | White | White | White |
| Aroma[2] | Sweet | Sweet | Sweet | Sweet | Sweet | Sweet | Sweet | Sweet | Sweet | Sweet |
| Flavor[2] | Sweet | Sweet | Sweet | Sweet | Sweet | Sweet | Sweet | Sweet | Sweet | Sweet |

[1]Leaf serration was graded on a 0-9 scale with scores of 0 indicating entire leaf margins and increasing scores for increasing degrees of serration.

[2]Sweet is a descriptor for the traditional sweet basil aroma and flavor.

TABLE 5

Flowering time by the new sweet basil cultivars as compared to commercial sweet basils which served as comparative controls (Thermal, CA. 2017).

| Days post sowing | Passion | Rutgers Devotion DMR | 26-24-33-05 | 42-21-01-02 | 50-03-34-05 | 47-08-23-02 | 07-73-02-05 | Commercial Standard 1 | Commercial Standard 2 |
|---|---|---|---|---|---|---|---|---|---|
| 70 | 0.01 | 0.38 | 0.39 | 0.00 | 0.00 | 0.05 | 0.01 | 0.36 | 0.01 |
| 75 | 0.39 | 0.57 | 0.85 | 0.39 | 0.00 | 0.40 | 0.28 | 0.97 | 0.14 |

BDM Disease Resistance/Tolerance

The tolerance of the new varieties to BDM was tested as follows. A mean disease score was assigned by taking the average score across three replicated plots in a single location on a single rating date. To provide a measure of response to disease over multiple rating dates, the unit of area under the disease progress curve (AUDPC) is most widely accepted in the plant sciences. AUDPC combines disease scores from multiple observations unto a single value using the equation:

$$AUDPC = \sum_{i=1}^{n}[(Y_{i+1}+Y_i)][(t_{i+1}-t_i)]$$

Where Y represents a rating score of the ith rating date and t represents the day of the ith rating date. A lower score indicates less disease severity of sporulation.

As a robust measure of disease severity, AUDPC among lines provides a relative comparison of the response to BDM among the sweet basil varieties described and two commercial control varieties.

As shown in Table 6, a mean AUDPC among the eight new varieties that is at least 3× less than either commercial standard. Thus, the eight varieties performed better than any of the commercial seed relative to the onset or expression of BDM infestation. All commercial sweet basils suffered from, and were significantly injured by, BDM while the new eight sweet basil cultivars produced healthy and fully marketable fresh crops with no marketable leaf loss due to BDM.

separated from the stems for hydro-distillation after drying. Essential oils were extracted by hydrodistillation using 100 g of dried leaves. They were distilled in a 2 L round bottom flask for 3 hours in 1 L of distilled water and the essential oil was collected in a Clevenger-type trap. The essential oils were then prepared and analyzed by GC/MS.

GC/MS Sample Preparation and Injection Conditions: Essential oil samples were prepared by the extraction 10 µL of crude sweet basil essential oil with 1.5 ml of TMBE which was then dried over anhydrous sodium sulfate and centrifuged at 13 Krpm. The supernatant was transferred to a sampling vial for analysis. Essential oil separation was done on a Shimadzu 2010 Plus gas chromatograph equipped with and AOC-6000 auto-sampler and the calculation of the relative abundance of compound fragments was performed on a Shimadzu TQ8040 MS.

The injection volume of 1 µL was separated on a H-Rxi-5Sil MS column heated from 35° C. with a hold of 4 min to 250° C. with a hold of 1.25 min at 20° C/min. The inlet temperature was 250° C. with a split less injection. The ion source temperature was set to 200° C., the interface temperature was set to 250° C., the solvent cut time was 3.5 min, and the detector voltage was set to 0.2 kV with a threshold of 1000. Peak integration percentages were calculated using the GCMSsolution v4.3© software from Shimadzu Corporation. Individual compound identities were determined by comparing the mass spectral results to current literature and screening them in the NIST05.LIB, NISTO5s.LIB, W10N14.lib and the W10N14R.lib mass spectral libraries.

Figure 5:
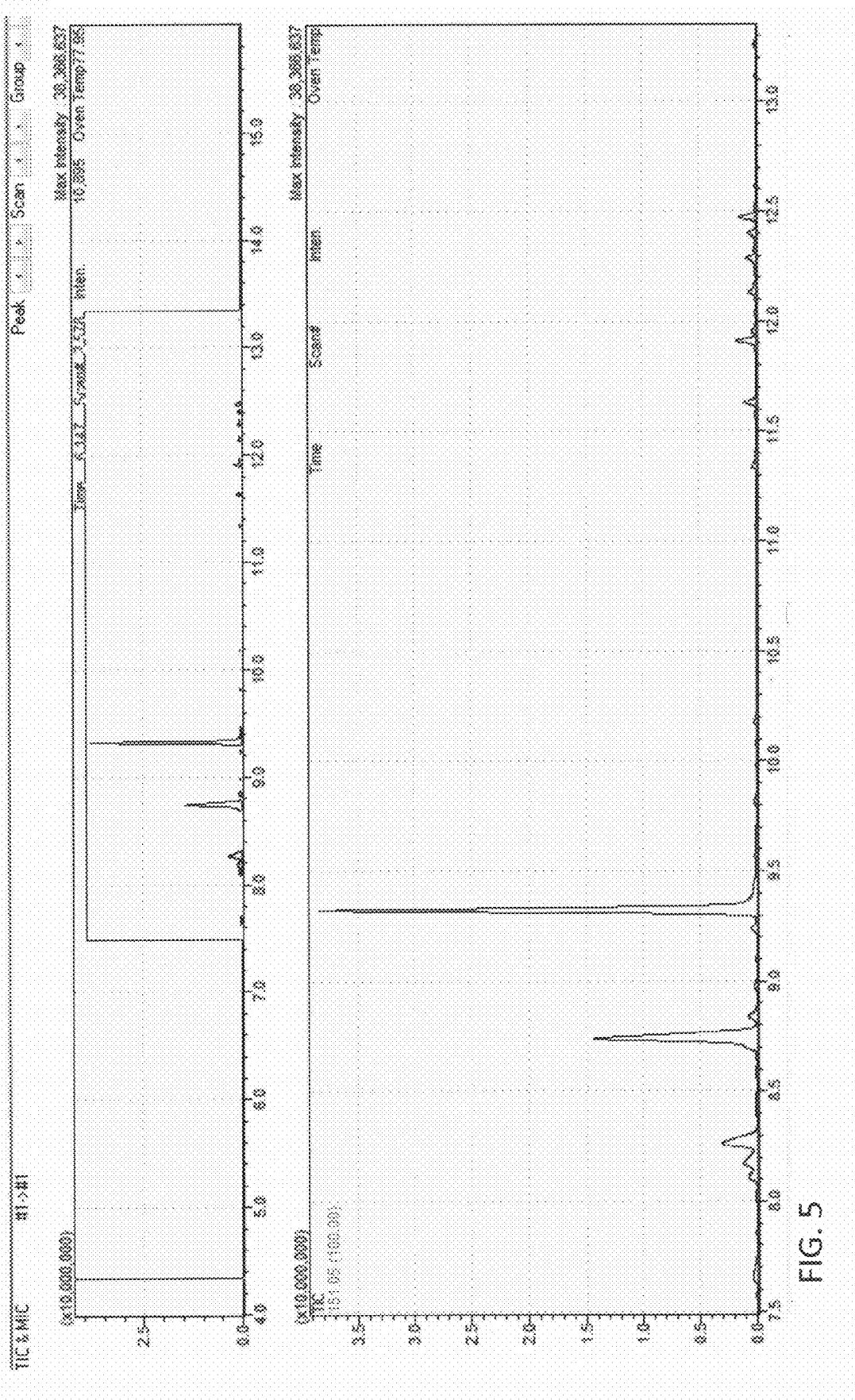
FIG. 5 illustrates in a pictorial manner (chromatogram) the aroma volatiles of the essential oils analyzed using gas chromatography and mass spec for fresh '47-21-07'.

FIG. 5 shows a representative sample chromatogram of the aroma volatiles of the essential oils for fresh '47-21-07'.

TABLE 6

Basil Downy Mildew response by the new sweet basil varieties during the 2017 New Jersey growing season*

| Location | Passion | Rutgers Devotion DMR | 26-24-33 | 42-21-02 | Obsession | 50-03-05 | 50-03-34 | Commercial Standard | Susceptible Control |
|---|---|---|---|---|---|---|---|---|---|
| Pittstown, NJ | 8.00 | 0.00 | 1.00 | 3.50 | 0.00 | 0.00 | 0.00 | 54.00 | 56.50 |
| Bridgeton, NJ | 29.38 | 4.75 | 8.88 | 4.75 | 33.25 | 0.00 | 0.88 | 54.50 | 63.75 |
| Mean | 18.69 | 2.38 | 4.94 | 4.13 | 16.63 | 0.00 | 0.44 | 54.25 | 60.13 |

*Values are in units of Area Under the Disease Progress Curve (AUDPC) calculated across three rating dates and three replications of a randomized complete block design in each location.

Oil Characterization

Cultivation and Essential Oil Preparation: The eight new basil varieties were grown in a randomized complete block experimental design with three replications. All eight varieties were grown from seed in greenhouse conditions and were transplanted to the field six weeks later. Each variety was harvested 65-75 days after seedlings, harvested and dried at 37° C. with an onsite Powell walk-in forced air heat dryer kept under low heat conditions. Dried leaves were Table 7 provides analysis of aromatic volatile compounds from dried leaf material. Table 8 provides analysis of aromatic volatile compounds from fresh leave material. Table 9 provides analysis of aromatic volatile compounds from the essential oil obtained from the leaves of the plants. The results indicate that the new sweet basil cultivars fall within the normative description of sweet basils (Lee et al., Perfumer & Flavorist 42:37-40,42-50, 2017).

TABLE 7

The major (>1%) aromatic volatile compounds from dried leaf material (GC/MS headspace) of the new sweet basil cultivars

| Component | RI | Passion | Rutgers Devotion DMR | 26-24-33 | 42-21-01 | 50-03-34 |
|---|---|---|---|---|---|---|
| RT:8.107 | 977 | 0.24 | 0.36 | 0.59 | 0.87 | 0.25 |
| pinene | 982 | 0.17 | 0.38 | 0.59 | 3.02 | 0.63 |
| myrcene | 990 | 5.99 | 5.34 | 5.11 | 4.84 | 4.86 |
| 1,8-cineole | 1038 | 6.34 | 7.51 | 7.69 | 33.15 | 7.44 |
| ocimene | 1048 | 1.98 | 2.10 | 1.25 | 1.17 | 2.11 |
| linalool | 1100 | 62.16 | 70.85 | 40.31 | 43.31 | 63.08 |
| RT:9.819 | 1159 | 0.22 | 0.61 | 4.14 | 0.31 | 1.84 |
| methyl chavicol | 1203 | 1.83 | 4.90 | 3.48 | 0.49 | 5.65 |
| RT:10.863 | 1294 | 1.70 | 0.36 | 0.51 | ND | 0.51 |
| RT:11.236 | 1349 | 0.32 | ND | 8.77 | 0.41 | 0.20 |
| eugenol | 1362 | 10.20 | 0.86 | 16.72 | 1.13 | 4.24 |
| elemene | 1404 | 1.19 | 0.64 | 1.94 | 2.34 | 1.42 |
| bergamotene | 1449 | 0.49 | 1.01 | ND* | 0.80 | 3.45 |
| humulene | 1482 | 0.77 | 0.28 | 0.69 | 0.47 | 0.84 |
| RT:12.290 | 1506 | 0.69 | 0.72 | 1.08 | 1.42 | 0.50 |
| RT:12.400 | 1535 | 2.79 | 1.96 | 3.35 | 4.20 | 1.52 |
| RT:13.262 | 1666 | 1.55 | 1.60 | 2.28 | 0.79 | 0.79 |

*ND = Not detected

TABLE 8

The major (>1%) aromatic volatile compounds from fresh leaf material (GC/MS headspace) of the new sweet basil cultivars

| Component | RI | Passion | Rutgers Devotion DMR | 26-24-33 | 42-21-01 | Obsession | 50-03-34 |
|---|---|---|---|---|---|---|---|
| RT:8.107 | 977 | 0.24 | 0.14 | 0.29 | 0.72 | 1.06 | 0.22 |
| pinene | 982 | 0.50 | 0.20 | 1.13 | 1.63 | 2.69 | 0.39 |
| myrcene | 990 | 6.31 | 3.70 | 4.88 | 4.17 | 8.82 | 6.56 |
| 1,8-cineole | 1038 | 8.29 | 2.37 | 14.06 | 18.75 | 22.86 | 7.77 |
| ocimene | 1048 | 0.83 | 1.48 | 1.03 | 1.98 | 1.31 | 1.02 |
| RT:9.238 | 1091 | 0.75 | 0.54 | 1.49 | 0.22 | 0.90 | 1.04 |
| linalool | 1100 | 60.36 | 79.60 | 48.46 | 58.61 | 50.69 | 59.95 |
| RT:9.819 | 1159 | 0.14 | 0.66 | 5.68 | 0.29 | 0.36 | 1.60 |
| methyl chavicol | 1203 | 0.25 | 0.12 | 0.77 | 1.92 | 0.35 | 0.21 |
| eugenol | 1362 | 6.96 | 0.12 | 2.93 | 5.04 | 1.13 | 2.47 |
| beta elemene | 1404 | 1.77 | 1.28 | 4.71 | 1.01 | 1.62 | 2.36 |
| bergamotene | 1449 | 1.24 | 3.67 | 1.22 | 0.26 | 2.45 | 9.33 |
| humulene | 1482 | 2.32 | 0.55 | 1.64 | 0.33 | 0.92 | 1.43 |
| RT:12.290 | 1506 | 2.32 | 1.31 | 1.98 | 0.85 | 0.87 | 1.32 |
| RT:12.400 | 1535 | 5.56 | 3.24 | 7.08 | 2.30 | 2.92 | 3.36 |
| RT:13.262 | 1666 | 0.60 | 0.65 | 1.83 | 1.27 | 0.78 | 0.75 |

ND = Not detected

TABLE 9

The major (>1%) aromatic volatile compounds from the essential oil of two of the new sweet basil cultivars.

| Component | RI | 42-21-01-02 | 50-03-34-05 |
|---|---|---|---|
| myrcene | 990 | 0.64 | 0.15 |
| 1,8-cineole | 1038 | 1.90 | 1.78 |
| linalool | 1100 | 69.13 | 51.90 |
| RT:9.819 | 1159 | ND | 2.17 |
| methyl chavicol | 1203 | 0.23 | 0.60 |
| RT:10.863 | 1294 | 2.19 | 0.17 |
| eugenol | 1362 | 10.04 | 8.54 |
| elemene | 1404 | 0.53 | 1.81 |
| bergamotene | 1449 | ND | 14.94 |
| humulene | 1482 | 1.60 | 3.11 |
| RT:12.290 | 1506 | 1.99 | 3.10 |

TABLE 9-continued

The major (>1%) aromatic volatile compounds from the essential oil of two of the new sweet basil cultivars.

| Component | RI | 42-21-01-02 | 50-03-34-05 |
|---|---|---|---|
| RT:12.400 | 1535 | 4.18 | 2.97 |
| RT:13.262 | 1666 | 6.94 | 8.05 |

ND = Not detected

EXAMPLE 4

Genetic Analysis

This example describes the genetic analysis of the eight new varieties: 'Thunderstruck', 'Passion', 'Obsession', 'Rutgers Devotion DMR', '26_24_33', '50_03_05', '50_03_34', and '42_21_02'. Additional details can be found in Pyne et al. (PLOS One 12:e0184319, 2017).

SSR Genotyping

Approximately 80 mg of young leaf tissue was collected from three full siblings of each variety ('Thunderstruck', 'Passion', 'Obsession', 'Rutgers Devotion DMR', '26_24_33', '50_03_05', '50_03_34', and '42_21_02'. Leaf tissue samples were ground in liquid nitrogen and genomic DNA (gDNA) was extracted using the E.N.Z.A. SP Plant DNA Kit (Omega BioTek, Norcross, Ga.). DNA was quantified and assessed for quality by measurement of 260/280 and 260/230 absorbance ratios using a Nanodrop (Thermo Scientific, Waltham, Mass.).

The National Center for Biotechnology Information (NCBI) *O. basilicum* expressed sequence tag (EST) database of 23,845 cDNA sequences was downloaded and assembled using CAP3 software with default settings. The resulting contig and remaining singlet sequences were mined with SciRoKo software for di-, tri- and tetranucleotide repeat sequences with a minimum of 10 nucleotides. SSRs meeting this criteria were selected for the presence of ≤300 bp flanking sequences that were subsequently used for primer pair design with Primer3 software. This produced 811 putative SSR markers from which a subset of 89 di-, 115 tri-, and 36 tetranucleotide were used. Primer pairs (Table 10) were synthesized (Integrated DNA Technologies, Coralville, Iowa) with the 5' end of forward primers appended with the M13 (−21) sequence (5'-TGTAAAACGACGGC-CAGT-3'; SEQ ID NO: 59) to facilitate fluorescent labeling of PCR products. The 5' end of reverse primers were "pig-tailed" with the 5'-GTTTCTT-3' sequence to ensure consistent polyadenylation across reactions.

PCR amplification for all reactions included 5 ng of gDNA, 10× Ramp-Taq PCR buffer (Denville Scientific, Metuchen, N.J.), 2.0 mM MgCl2, 0.25 mM each dNTP (Denville Scientific), 0.5 U Ramp-Taq DNA polymerase (Denville Scientific), 0.5 pmol forward primer, 1.0 pmol reverse primer, and 1.0 pmol fluorescently labeled (FAM, NED, PET, or VIC) M13(−21) primer. Template gDNA was amplified using the following conditions: initial denaturation of 94° C. for 5 min, followed by 30 cycles of 94° C. for 30 sec, 55° C. for 45 sec, 72° C. for 45 sec, followed by 20 cycles of 94° C. for 30 sec, 53° C. for 45 sec, 72 C for 45 sec, followed by a final extension of 72° C. for 10 min. GeneScan 600 LIZ (Applied Biosystems) size standard was added to resulting PCR products and separated by capillary electrophoresis on an ABI 3500xL Genetic Analyzer (Life Technologies Corporation, Carlsbad, Calif.). PCR product fragment length measurement and allele binning and was performed using Genemapper 4.1 software (Applied Biosystems).

SSR fragment lengths (nucleotides) are shown in Tables 11-15.

TABLE 10

SSR primer sequences and repeat motif used to genotype the new varieties. SEQ ID NO: is shown after the sequence.

| MarkerID | Primer Sequence (5' -> 3')[1] | Reverse Sequence (5' -> 3')[1] | Repeat Motif |
|---|---|---|---|
| OBNJR2cn17 | CTAGAGCTAGCGCAGGATGC (1) | GATCGTCCGGTATTGCAGA (2) | (AT)10 |
| OBNJR2cn38 | TCACGGTCAGCTCTCTCTCTC (3) | CACACCGCTGAGTTTGAGAA (4) | (CA)13 |
| OBNJR2cn73 | TAAGCCCTTTGGTCATCCAC (5) | CAAGGACAATTCCTATTTAGTTCCA (6) | (CT)24 |
| OBNJR2cn79 | GGCGATGCTGGAGAACATT (7) | GGAAAGTAGATCCGAGAGGGA (8) | (AT)9 |
| OBNJR2cn80 | ATTTCAGCGCTCACATGACA (9) | AGGAGCTGGATGGAAAGTCA (10) | (TA)12 |
| OBNJR2cn83 | CTTCCGCAATCAGAAGAAGC (11) | TGAATTTGTAGCGCACTTCG (12) | (GA)18 |
| OBNJR2cn92 | TGACATCAGCTCCAGAATGC (13) | ACCCATATTTCGCCTTCTCA (14) | (CT)13 |
| OBNJR3cn358 | TGCTTTAGCCGGAGTGATCT (15) | CAGCAGCAAATCCAAGTCAA (16) | (TCC)7 |
| OBNJR2sg15 | CAACTGCTAGTCGTGGGACA (17) | CGACTCATGACCAGTAAACCTG (18) | (GA)25 |
| OBNJR2sg21 | TTTGCTCTGCTGGAGGGTAT (19) | CAACAGGCATCGAAGTAGCA (20) | (TC)13 |
| OBNJR2sg31 | CTTGAATTCGCGCAGTATGA (21) | AAACAGCGGATTCACCACTC (22) | (AG)9 |
| OBNJR2sg34 | CCCAGGATTATTCCCTCATT (23) | GAACATGGGAGGGATGAAGA (24) | (CT)11 |
| OBNJR3cn80 | TCGTCTTCGAACATGAGACG (25) | AAATGTCAGCTTTCATCGCC (26) | (GGC)5 |
| OBNJR3cn201 | GCAGCAGCATTCAGGTACAA (27) | GGGAGATTATTCACGAGGCA (28) | (GAA)6 |
| OBNJR3cn217 | ACTCCTTATGCTGGGACCCT (29) | TCGTGCAGGAATGTGAAATC (30) | (ATT)6 |
| OBNJR3cn239 | CAAGGCAGCACAACATTCAG (31) | AATGGCGTCTACCTTTGTGG (32) | (TTC)8 |
| OBNJR3cn328 | CGTACAGCAGCAGTAGCAGC (33) | GCTGCATTTGTGAACTGCTC (34) | (AAG)6 |
| OBNJR3cn356 | TGGAGGGAGAAGGTGAGAAA (35) | TCCTTGCTGTGTTCCTTTCC (36) | (AAG)9 |
| OBNJR3cn391 | CCCACCTCATCTTCTCATGG (37) | CAGCTTGAAGTAGCCCTTGG (38) | (TCA)5 |
| OBNJR3cn401 | ACCTGTAAACCAGCACCACC (39) | TGACATGGGAGGAGGAACTC (40) | (CAG)7 |
| OBNJR3sg98 | ACCAAATCCAAGACCCTCCC (41) | TTGTAGAAGAGGCTCGTCGG (42) | (CCT)8 |
| OBNJR3sg137 | TTGTGTGGATTGCGGTTAAA (43) | CGGACCTTACTTCATTCGGA (44) | (TCA)6 |
| OBNJR4cn10 | CACGACATATAAGCGCGATG (45) | TCTGCTGGTGATGAGCTGTC (46) | (AACA)4 |
| OBNJR4cn11 | CTGTCATCGCCACAAGCTAA (47) | TTGTGGCGCTTGAGAAGTTA (48) | (TCAC)4 |
| OBNJR4cn14 | CACAACATGAACAAAGACCCA (49) | AGTGGAATCCGAAGCATTTG (50) | (TAGA)4 |
| OBNJR4cn15 | CAGCATCTCCGAACTGTGAA (51) | AAACGATCATCTCCTCCACG (52) | (GCCT)5 |
| OBNJR4cn16 | TTCACTCTGCCAGGCCTAAT (53) | CTGTTTGAGCTGTGACGGAA (54) | (CAAA)4 |
| OBNJR4sg01 | CAAACTTCAACCTCAACATTCAA (55) | GAGGAGGAGGAGGAAGAGGA (56) | (TCCC)5 |
| OBNJR4sg06 | CAAAGAGCCAATTAGTTTCCC (57) | AGGCGACGGATTCATAGTTG (58) | (ACAA)5 |

[1]The 5' end of forward primers were appended with the M13 (−21) sequence (5'-TGTAAAACGACG-GCCAGT-3'; SEQ ID NO: 59) and reverse primers were "pig-tailed" with the 5'-GTTTCTT-3' sequence.

TABLE 11

| | SSR fragment lengths (nucleotides) | | | | | | | | |
|---|---|---|---|---|---|---|---|---|---|
| | Passion | | | Rutgers Devotion DMR | | | 26-24-33 | | |
| Full Sibling | 1 | 2 | 3 | 1 | 2 | 3 | 1 | 2 | 3 |
| OBNJR2cn17 | NA | NA | 179, 185 | 179, 185 | 179, 185 | 179, 185 | 179, 185 | 179, 185 | 179, 185 |
| OBNJR2cn38 | 171 | 171 | 171 | 171 | 171 | 171 | 171 | 171 | 171 |
| OBNJR2cn73 | 257 | 257 | 257 | 257 | 257 | NA | 257 | 257 | 257 |
| OBNJR2cn79 | 271 | 271 | 271 | 271 | 271 | 271 | 271 | 271 | 271 |
| OBNJR2cn80 | 226, 229 | 226, 229 | 226, 229 | 226, 229 | 226, 229 | 226, 229 | 226, 229 | 226, 229 | 226, 229 |
| OBNJR3cn83 | 181 | 175 | 175 | 175 | 175 | 175 | 175 | 175 | 175 |
| OBNJR2cn92 | 255 | 255 | 255 | 263 | 263 | 263 | 255 | 255 | 255 |
| OBNJR2cn358 | 399, 401 | 399, 401 | 399, 401 | 392, 401 | 392, 401 | 392, 401 | 399, 401 | 399, 401 | 399, 401 |
| OBNJR2sg15 | 187 | 187 | 187 | 187 | 187 | 187 | NA | 187 | 187 |
| OBNJR2sg21 | 268 | 268 | 268 | 268 | 268 | NA | 268 | 268 | 268 |
| OBNJR2sg31 | 248, 263, 265 | 248, 263, 265 | 248, 263, 265 | 248, 262, 263 | NA | 248, 262 | 248,, 263, 269 | 248, 269 | 248, 269 |

TABLE 11-continued

| | SSR fragment lengths (nucleotides) | | | | | | | | |
|---|---|---|---|---|---|---|---|---|---|
| | Passion | | | Rutgers Devotion DMR | | | 26-24-33 | | |
| Full Sibling | 1 | 2 | 3 | 1 | 2 | 3 | 1 | 2 | 3 |
| OBNJR2sg34 | 194 | 194 | 194 | 194 | 194 | 194 | NA | 194 | 194 |
| OBNJR3cn80 | 204 | 195, 204 | 195 | 204 | 204 | 204 | 204 | 204 | 204 |
| OBNJR3cn201 | 273, 291 | 273, 291 | 273, 291 | 273, 291 | 273, 291 | 273, 291 | 273, 282, 291 | 273, 282, 291 | 282, 291 |
| OBNJR3cn217 | 292, 299 | 292, 299 | 299 | 299 | 299 | 292, 299 | 292, 299 | 292, 299 | 292, 299 |
| OBNJR3cn239 | 319 | 319 | 319 | 319 | 319 | 319 | 319 | 319 | 319 |
| OBNJR3cn328 | 229, 232, 253, 256, | 229, 232, 253, 256 | 229, 232, 253, 259 | 229, 232, 253, 256, 259 | 229, 232, 253, 256, | 253, 256 | 229, 232, 253, 259, 262 | 229, 232, 253, 259 | 229, 232 253, 259, 262 |
| OBNJR3cn356 | 313, 316 | 313, 316 | 313, 316 | 313, 316 | 313, 316 | 313, 316 | 313, 316, 342 | 313, 316 | 313, 316, 342 |
| OBNJR3cn391 | NA | NA | 188 | 185, 188 | 185, 188 | 184 | 185, 188 | 185, 188 | 185, 188 |
| OBNJR3cn401 | 263 | 263 | 263 | 255, 263 | 255, 263 | 255, 263 | 255, 263 | 255, 263 | 255, 263 |
| OBNJR3sg98 | 152, 161 | 161 | 152, 161 | 152, 161 | 152, 161 | 152, 161 | 152, 155, 161 | 152, 155, 161 | 152, 155, 161 |
| OBNJR3sg137 | 574, 584 | 574, 584 | 574, 584 | 571, 574, 584 | 571, 574, 584 | 571, 584 | 574, 584 | 574, 584 | 574, 584 |
| OBNJR4cn10 | 157, 178 | 157, 178 | 178 | 160, 178 | 160, 178 | 160, 178 | 157, 178 | 157, 178 | 157, 178 |
| OBNJR4cn11 | 227 | 227 | 227 | 227 | 227 | 227 | 227 | 227 | 227 |
| OBNJR4cn14 | 267 | 267 | 267 | 263, 267 | 263, 267 | 263, 267 | 267 | 267 | 267 |
| OBNJR4cn15 | 347, 352 | 347, 352 | 347, 352 | 343, 352 | 343, 352 | 343, 352 | 347, 352 | 347, 352 | 347, 352 |
| OBNJR4cn16 | 218, 109 | 218, 109 | 218, 109 | 218, 109 | 217, 218, 109 | 218, 109 | 217, 109 | 217, 109 | 217, 109 |
| OBNJR4sg01 | 109, 170 | 109, 170 | 109, 170 | 109, 170 | 109, 170 | 109, 170 | 109, 170 | 109, 170 | 109, 170 |
| OBNJR4sg06 | NA | NA | 239 | 239, 242 | 239, 242 | 239, 242 | 239, 242 | 239, 242 | 239, 242 |

TABLE 12

| | SSR fragment lengths (nucleotides) | | | | | | | | |
|---|---|---|---|---|---|---|---|---|---|
| | 42-21-02 | | | 47-08-23 | | | Obsession | | |
| Full Sibling | 1 | 2 | 3 | 1 | 2 | 3 | 1 | 2 | 3 |
| OBNJR2cn17 | 179, 185 | 179, 185 | 179, 185 | NA | 179, 185 | 179, 185 | 179, 185 | 179, 185 | 179, 185 |
| OBNJR2cn38 | 171 | 171 | 171 | 171 | NA | 171 | 171 | 171 | 171 |
| OBNJR2cn73 | 257 | 257 | 257 | 257 | NA | 257 | 257 | 257 | 257 |
| OBNJR2cn79 | 271 | 271 | 271 | 271, 275 | 271, 275 | 271, 275 | 271 | 271 | 271 |
| OBNJR2cn80 | 226, 229 | 226, 229 | 226, 229 | 226, 229 | 226, 229 | 226, 229 | 226, 229 | 226, 229 | 226, 229 |
| OBNJR2cn83 | 175, 181 | 175, 181 | 175, 181 | 175 | 175 | 175 | 175 | 175 | 175 |
| OBNJR2cn92 | 255 | 255 | 255 | 255 | 255 | 255 | 263 | 263 | 263 |
| OBNJR2cn358 | 392, 401 | 401 | 401 | 399, 401 | 399, 401 | 399, 401 | 401 | 399, 401 | 399, 401 |
| OBNJR2sg15 | 183 | 187 | 187 | 187 | 187 | 187 | 187 | 187 | 187 |
| OBNJR2sg21 | 268 | 268 | 268 | 268 | 268 | 268 | 268 | 268 | 268 |
| OBNJR2sg31 | 248, 265 | 248, 263, 265 | NA | 248, 262 | 248, 262 | 248, 262 | 248, 263, 265 | 248, 263, 265 | 248, 263, 265 |
| OBNJR2sg34 | 194 | 194 | 194 | 194 | 194 | 194 | 194 | 194 | 194 |
| OBNJR3cn80 | 195 | 195 | NA | 204 | 204 | 204 | 195 | 195, 204 | 195 |
| OBNJR3cn201 | 273, 291 | 273, 291 | 273, 291 | 273, 291 | 273, 291 | 273, 291 | 273, 291 | 273, 291 | 273, 291 |

TABLE 13

| | SSR fragment lengths (nucleotides) | | | | | | | | |
|---|---|---|---|---|---|---|---|---|---|
| | 42-21-02 | | | 47-08-23 | | | Obsession | | |
| Full Sibling | 1 | 2 | 3 | 1 | 2 | 3 | 1 | 2 | 3 |
| OBNJR3cn217 | 299 | 299 | 299 | 292, 299 | 292, 299 | 292, 299 | 292, 299 | 292, 299 | 292, 299 |
| OBNJR3cn239 | 319 | 319 | 319 | 319 | 319 | 319 | 319 | 319 | 319 |
| OBNJR3cn328 | 229, 232, 253, 259 | 229, 232, 253, 259 | 229, 232, 253, 259 | 229, 232, 253, 256 | 229, 232, 253, 256 | 229, 232, 253, 256 | 229, 232, 253, 259 | 229, 232, 253, 259 | 229, 232, 253, 259 |
| OBNJR3cn356 | 310, 342 | 310, 342 | 310, 342 | 313, 342 | 313, 342 | 310, 316 | 310, 316 | 313, 316 | 310, 316 |
| OBNJR3cn391 | 184, 188 | 184, 188 | 184, 188 | 185, 188 | 185, 188 | 185, 188 | 184, 185, 188 | NA | NA |
| OBNJR3cn401 | 263 | 263 | 263 | NA | 255, 263 | 255, 263 | 260, 263 | 263 | 263 |
| OBNJR3sg98 | 152, 161 | 152, 161 | 152, 161 | 152, 161 | 152, 161 | 152, 161 | 152, 161 | 152, 161 | 152, 161 |
| OBNJR3sg137 | 574, 584 | 574, 584 | 574, 584 | 571, 584 | 571, 584 | 571, 584 | 574, 584 | 574, 584 | 574, 584 |
| OBNJR4cn10 | 160, 178 | 160, 178 | 160, 178 | 157, 178 | 157, 178 | 157, 178 | 157, 178 | 157, 178 | 157, 178 |

TABLE 13-continued

| | SSR fragment lengths (nucleotides) | | | | | | | | |
|---|---|---|---|---|---|---|---|---|---|
| | 42-21-02 | | | 47-08-23 | | | Obsession | | |
| Full Sibling | 1 | 2 | 3 | 1 | 2 | 3 | 1 | 2 | 3 |
| OBNJR4cn11 | 227, 235 | 227, 235 | 227, 235 | 227 | 227 | 227 | 227 | 227 | 227 |
| OBNJR4cn14 | 267 | 267 | 267 | 263, 267 | 263, 267 | 263, 267 | 267 | 267 | 267 |
| OBNJR4cn15 | 347, 352 | 347, 352 | 347, 352 | 347, 352 | 347, 352 | 347, 352 | 347, 352 | 347, 352 | 347, 352 |
| OBNJR4cn16 | 217, 109 | 217, 109 | 217, 109 | 218, 109 | 218, 109 | 218, 109 | 217, 218, 109 | 217, 218, 109 | 218, 109 |
| OBNJR4sg01 | 109, 170 | 109, 170 | 109, 170 | 109, 170 | 109, 170 | 109, 170 | 109, 170 | 109, 170 | 109, 170 |
| OBNJR4sg06 | 239 | 239 | 239 | NA | 239, 242 | 239, 242 | 242 | 242 | 242 |

TABLE 14

| | SSR fragment lengths (nucleotides) | | | | | | | | |
|---|---|---|---|---|---|---|---|---|---|
| | 50-03-34 | | | 50-03-05 | | | Caesar | Digenova | Eleonora |
| Full Sibling | 1 | 2 | 3 | 1 | 2 | 3 | 1 | 1 | 1 |
| OBNJR2cn17 | 179, 185 | 179, 185 | NA | 179, 185 | 179, 185 | 179, 185 | 185 | 185 | 185 |
| OBNJR2cn38 | 171 | 171 | 171 | 171 | 171 | 171 | 171 | 171 | 171 |
| OBNJR2cn73 | 257 | 257 | 257 | 257 | 257 | 257 | 257 | 257 | 251 |
| OBNJR2cn79 | 271 | 271 | 271 | 271 | 271 | 271 | 271 | 271 | 271 |
| OBNJR2cn80 | 226, 229 | 226, 229 | 226, 229 | 226, 229 | 226, 229 | 226, 229 | 226, 229 | 226, 229 | 226, 229 |
| OBNJR2cn83 | 175 | 175 | 175 | 175, 181 | 175, 181 | 175, 181 | 175, 181 | 175 | 175 |
| OBNJR2cn92 | 255 | 255 | 255 | 255 | 255 | 255 | 255 | 255 | 255 |
| OBNJR2cn358 | 392, 401 | 392, 401 | 392, 401 | 392, 401 | 392, 401 | 392, 401 | 399, 401 | 399 | NA |
| OBNJR2sg15 | 187 | NA | 187 | 187 | 187 | 187 | 181, 183, 185, | 183 | 185 |
| OBNJR2sg21 | NA | 268 | 268 | 268 | 268 | 268 | 268 | 266 | 268 |
| OBNJR2sg31 | 248, 269 | 248, 269 | 248, 269 | 248, 269 | 248 | 248 | 248, 263 | 248, 269 | 248, 262 |
| OBNJR2sg34 | 194 | 194 | 194 | 194 | 194 | 194 | 194 | 198 | 212 |
| OBNJR3cn80 | 195 | 195, 204 | 195 | 195 | 195 | 195 | 204 | 204 | 195 |
| OBNJR3cn201 | 273, 282 | 273, 282 | 273, 282 | 273, 282 | 273, 282 | 273, 282 | 273, 291 | 273, 291 | 270, 273, 291 |

TABLE 15

| | SSR fragment lengths (nucleotides) | | | | | | | | |
|---|---|---|---|---|---|---|---|---|---|
| | 50-03-34 | | | 50-03-05 | | | Caesar | Digenova | Eleonora |
| Full Sibling | 1 | 2 | 3 | 1 | 2 | 3 | 1 | 1 | 1 |
| OBNJR3cn217 | 292, 299 | NA | 292, 299 | 292, 299 | 292, 299 | 292, 299 | 292, 299 | 292, 299 | 292, 299 |
| OBNJR3cn239 | 319 | 319 | 319 | 319 | 319 | 319 | 319 | 319 | 319 |
| OBNJR3cn328 | 229, 232, 253, 262 | 229, 232, 253, 262 | 229, 232, 253, 262 | 229, 232, 253, 262 | 229, 232, 253, 262 | 229, 232, 253, 262 | 229, 250, 259 | 229, 232, 250, 262 | 229, 232, 250, 259 |
| OBNJR3cn356 | 310, 316 | 310, 316 | 310, 316 | 310, 316 | 310, 316 | 310, 342 | 310, 316 | 310, 342 | 313, 342 |
| OBNJR3cn391 | NA | 184, 188 | 184, 188 | 184, 188 | 184, 188 | 184 | 188 | 188 | 185, 188 |
| OBNJR3cn401 | 255, 263 | 263 | 255, 263 | 263 | 263 | 263 | 255, 263 | 255, 263 | 260, 263 |
| OBNJR3sg98 | 152, 155, 161 | 152, 155, 161 | 152, 155, 161 | 152, 161 | 152, 155, 161 | 152, 155, 161 | 152, 161 | 152, 161 | 152, 161 |
| OBNJR3sg137 | 571, 584 | 571, 584 | 571, 584 | 571, 584 | 571, 584 | 571, 584 | 571, 574, 584 | 571, 584 | 571, 584 |
| OBNJR4cn10 | 160, 178 | 160, 178 | 160, 178 | 160, 178 | 160, 178 | 160, 178 | 160, 178 | 160, 178 | 160, 178 |
| OBNJR4cn11 | 227 | 227 | 227 | 227, 235 | 227, 235 | 227, 235 | 227, 235 | 227 | 227, 235 |
| OBNJR4cn14 | 263, 267 | 263, 267 | 263, 267 | 263, 267 | 263, 267 | 263, 267 | 263, 267 | 263, 267 | 263, 267 |
| OBNJR4cn15 | 343, 352 | 343, 352 | 343, 352 | 343, 352 | 343, 352 | 343, 352 | 347, 352 | 347, 352 | NA |
| OBNJR4cn16 | 218, 109 | 218, 109 | 217, 109 | 217, 218, 109 | 217, 218, 109 | 217, 218, 109 | 218 | 218 | 218 |
| OBNJR4sg01 | 109, 170 | 109, 170 | 109, 170 | 109, 170 | 109, 170 | 109, 170 | 117, 178 | 117, 178 | 117, 178 |
| OBNJR4sg06 | 242 | 242 | NA | 242 | 242 | 242 | 239, 242 | 239, 242 | 239, 242 |

Clustering Analysis

To provide a measure genetic relatedness between and purity within varieties 'Thunderstruck', 'Passion', 'Obsession', 'Rutgers Devotion DMR', '26_24_33', '50_03_05', '50_03_34', and '42_21_02' cluster analysis was performed using SSR genotype data from these and additional commercial varieties as well as outgroup accession CR9 (*Nepata cataria*). A Nei genetic distance matrix was first calculated using the binary genotype matrix and used as an input file for unweighted pair group method using arithmetic average (UPGMA) clustering was performed with Numerical Taxonomy System (NTSYSpc) ver 2.21q software (Exeter Software, Setauket, N.Y., USA). A genetic similarity matrix was generated using the Jaccard similarity coefficient method in the NTSYSpc SIMQUAL module. Cluster analysis was then performed by UPGMA in the SAHN module and the output was visualized as a dendrogram with the TREE module. A Mantel test was performed with 999 test permutations using the MXCOMP module to determine goodness of fit between the genetic similarity matrix and the UPGMA dendrogram converted to cophenetic values with the COPH module. Finally, the original binary genotype matrix was resampled 1,000 times using the RESAMPLE module and the results were used as input for the CONSENS module to calculate bootstrap values using the majority rule method and a minimum support value of 0.500.

Figure 6:
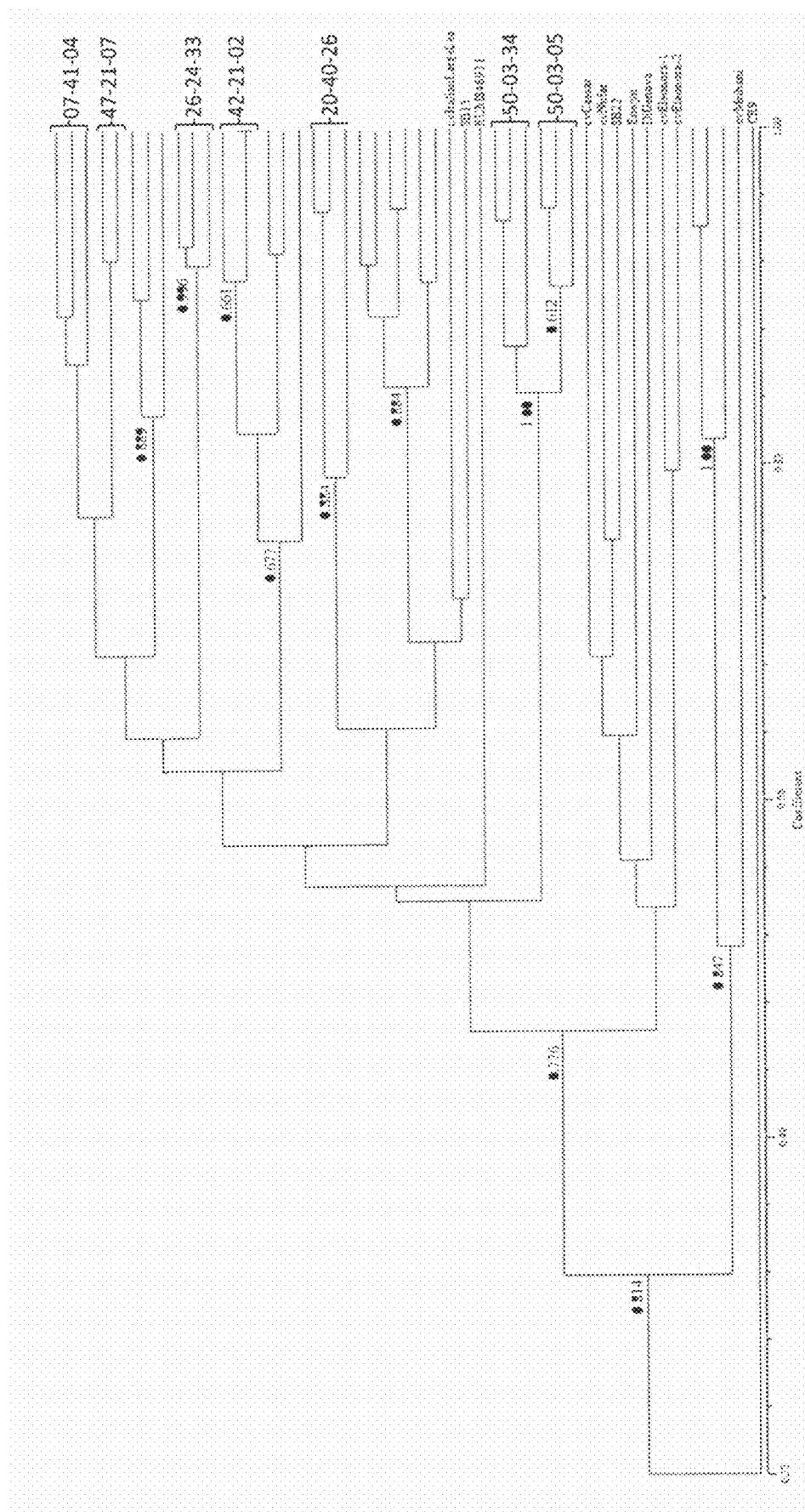
FIG. 6 is a visual representation (dendrogram) of genetic distance among the new sweet basil cultivars 'Thunderstruck', 'Passion', 'Obsession', 'Rutgers Devotion DMR', '26_24_33', '50_03_05', '50_03_34', and '42_21_02', additional Rutgers breeding lines and commercial varieties. The new cultivars group together demonstrating homogeneity within lines and distinctness from other commercially available lines. Unweighted pair group method using arithmetic average (UPGMA) dendrogram was used. Genetic distance was calculated using the Jaccard Similarity Coefficient (x-axis) and bootstrap values are the result of a 1,000 permutations with support value greater than 0.500 shown.

Results of this cluster analysis demonstrate full siblings for each variety form distinct clades as shown in FIG. 6. Genetic distance within DMR varieties is clearly lower than distance among said varieties. In multiple cases bootstrap support values exceed 0.500 and are as high as 0.996 for variety '26-24-33'.

The clustering also demonstrates the ability for this SSR marker set to discriminate among closely related groups of individuals such as the varieties described in this patent. Inclusion of major commercial varieties and their resolution as being genetically distinct from the DMR varieties shows their utility in distinguishing DMR varieties from other commercial varieties.

EXAMPLE 5

Chill Tolerance

This example describes the observed cold/chill tolerance for some of the new varieties.

Stems of the new basil plants were collected in Florida or NJ. Stems were placed upright in glasses of water at temperatures in the 70° 's F. No chill damage was observed.

Leaves/stems of the new basil plants were placed in a typical clam shell or plastic bag common in the fresh cut industry and placed in a refrigerator (at about 39-40° F.). Some leaves/stems of the new basil plants were placed in a small bowl, which was placed in a refrigerator (at about 39-40° F. with thermometer placed in the refrigerator adjacent to the sweet basil samples). Leaves/stems of the new basil plants were observed over 4-6 days, and it was observed that the plant material did not turn black, a sign of chill damage. Typically, unprotected fresh basil turns black at temperatures around 50° F. in 24 hours, while basil protected in clam shells or plastic bags would show chill damage at temperatures around 46° F. in 24 hours.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A plant of sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02', wherein representative seed of said variety have been deposited under American Type Culture Collection (ATCC) Accession No. PTA-124576, PTA-124574, PTA-124572, PTA-124578, PTA-124575, PTA-124573, PTA-124571, and PTA-124577, respectively.

2. A plant part of the plant of claim 1, wherein the plant part comprises
an embryo of said plant, or
at least one cell of said plant.

3. The plant part of claim 2, wherein the plant part is pollen, a meristem, a cell, an ovule, a leaf, a root, a root tip, a pistil, an anther, a protoplast, or a cotyledon.

4. A tissue culture produced from the protoplast or the cell of claim 3.

5. The tissue culture of claim 4, wherein the cell or protoplast is produced from a leaf, stem, protoplast, pollen, ovule, cotyledon, hypocotyl, meristematic cell, root, root tip, pistil, anther, flower, seed, shoot, stein, pod or petiole.

6. A sweet basil plant regenerated from the tissue culture of claim 4, wherein the regenerated sweet basil plant comprises all of the physiological and morphological characteristics of the sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02'.

7. A seed of sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02', wherein representative seed of said variety have been deposited under ATCC Accession No. PTA-124576, PTA-124574, PTA-124572, PTA-124578, PTA-124575, PTA-124573, PTA-124571, and PTA-124577, respectively.

8. A seed mixture, comprising the seed of claim 7.

9. A composition comprising the seed of claim 7 and plant seed growth media.

10. The composition of claim 9, wherein the plant seed growth media is soil or a synthetic cultivation medium.

11. A method of producing sweet basil seed, comprising crossing the plant of claim 1 with itself or a second sweet basil plant.

12. The method of claim 11, wherein the second sweet basil plant is transgenic.

13. An $F_1$ sweet basil seed produced by the method of claim 11.

14. A sweet basil plant or part thereof produced by growing the seed of claim 13, wherein the part thereof is pollen, a meristem, a cell, an ovule, a leaf, a root, a root tip, a pistil, an anther, a protoplast, or a cotyledon.

15. A plant of sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02', wherein representative seed of said variety have been deposited under American Type Culture Collection (ATCC) Accession No. PTA-124576, PTA-124574, PTA-124572, PTA-124578, PTA-124575, PTA-124573, PTA-124571, and PTA-124577, respectively, further comprising a single locus conversion introduced by backcrossing or transformation.

16. The plant of claim 15, wherein the single locus conversion comprises a transgene.

17. A seed that produces the plant of claim 15.

18. The seed of claim 17, wherein the single locus confers a trait selected from the group consisting of male sterility, herbicide tolerance, insect resistance, pest resistance, disease resistance, modified fatty acid metabolism, abiotic stress resistance, altered seed amino acid composition, site-specific genetic recombination, and modified carbohydrate metabolism.

19. The method of claim 11, wherein the method further comprises:
(a) crossing a plant grown from said sweet basil seed with itself or a different sweet basil plant to produce a seed of a progeny plant of a subsequent generation;
(b) growing a progeny plant of a subsequent generation from said seed of a progeny plant of a subsequent generation and crossing the progeny plant of a subsequent generation with itself or a second plant to produce a progeny plant of a further subsequent generation; and
(c) repeating steps (a) and (b) using said progeny plant of a further subsequent generation from step (b) in place of the plant grown from said sweet basil seed in step (a), wherein steps (a) and (b) are repeated with sufficient inbreeding to produce an inbred sweet basil plant derived from the sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02'.

20. The method of claim 19, further comprising crossing said inbred sweet basil plant derived from the sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02' with a plant of a different genotype to produce a seed of a hybrid sweet basil plant derived from the sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02'.

21. A method of producing a commodity plant product, the method comprising collecting or producing the commodity plant product from the plant of claim 1 or a part of the plant.

22. The method of claim 21, wherein the commodity plant product comprises a protein concentrate, protein isolate, biomass, leaves, extract, or oil.

23. A sweet basil commodity plant product produced by the method of claim 21, wherein the commodity plant product comprises at least one cell of and/or the genomic DNA of sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02'.

24. An extract or oil product of the plant of claim 1 or a part of the plant, wherein the extract or oil product comprises at least one cell of and/or the genomic DNA of sweet basil variety 'Rutgers Thunderstruck-DMR', 'Rutgers Passion-DMR', Rutgers Obsession-DMR', 'Rutgers Devotion-DMR', '26_24_33', '50_03_05', '50_03_34', or '42_21_02'.

25. A sweet basil plant produced by transforming the sweet basil plant of claim 1 with a transgene that confers upon the sweet basil plant to a desired trait, wherein the desired trait is one or more of herbicide tolerance, drought tolerance, heat tolerance, low or high soil pH level tolerance, salt tolerance, resistance to an insect, resistance to a bacterial disease, resistance to a viral disease, resistance to a fungal disease, resistance to a nematode, resistance to a pest, male sterility, site-specific recombination; abiotic stress tolerance, modified phosphorus characteristics, modified antioxidant characteristics; modified essential seed amino acid characteristics, decreased phytate, modified fatty acid metabolism, and modified carbohydrate metabolism.

26. A sweet basil seed produced by crossing two sweet basil plants and harvesting the resultant sweet basil seed, wherein at least one of the two sweet basil plants is the sweet basil plant of claim 1.

27. A container, comprising dried, frozen, and/or fresh leaves of the plant of claim 1.

28. A container, comprising the oil or extract of claim 24.

29. A method of producing a new sweet basil cultivar, comprising selecting a somaclonal variant of the plant of claim 1.

30. A method of producing a new sweet basil cultivar, comprising selecting a somaclonal variant of the of the tissue culture of claim 4.

* * * * *

SEQUENCE LISTING

```
<160> NUMBER OF SEQ ID NOS: 59

<210> SEQ ID NO 1
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2cn17

<400> SEQUENCE: 1
ctagagctag cgcaggatgc                                                 20

<210> SEQ ID NO 2
<211> LENGTH: 19
<212> TYPE: DNA
<213> ORGANISM: Artificial Sequence
<220> FEATURE:
<223> OTHER INFORMATION: Reverse primer sequence for marker ID:
      OBNJR2cn17

<400> SEQUENCE: 2
gatcgtccgg tattgcaga                                                  19

<210> SEQ ID NO 3
<211> LENGTH: 21
<212> TYPE: DNA
<213> ORGANISM: Artificial Sequence
<220> FEATURE:
<223> OTHER INFORMATION: Forward primer sequence for marker ID:
      OBNJR2cn38

<400> SEQUENCE: 3
```

```
tcacggtcag ctctctctct c                                              21
```

<210> SEQ ID NO 4
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR2cn38

<400> SEQUENCE: 4

```
cacaccgctg agtttgagaa                                                20
```

<210> SEQ ID NO 5
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2cn73

<400> SEQUENCE: 5

```
taagcccttt ggtcatccac                                                20
```

<210> SEQ ID NO 6
<211> LENGTH: 25
<212> TYPE: DNA
<213> ORGANISM: Artificial Sequence
<220> FEATURE:
<223> OTHER INFORMATION: Reverse primer sequence for marker ID:
      OBNJR2cn73

<400> SEQUENCE: 6

```
caaggacaat tcctatttag ttcca                                          25
```

<210> SEQ ID NO 7
<211> LENGTH: 19
<212> TYPE: DNA
<213> ORGANISM: Artificial Sequence
<220> FEATURE:
<223> OTHER INFORMATION: Forward primer sequence for marker ID:
      OBNJR2cn79

<400> SEQUENCE: 7

```
ggcgatgctg gagaacatt                                                 19
```

<210> SEQ ID NO 8
<211> LENGTH: 21
<212> TYPE: DNA
<213> ORGANISM: Artificial Sequence
<220> FEATURE:
<223> OTHER INFORMATION: Reverse primer sequence for marker ID:
      OBNJR2cn79

<400> SEQUENCE: 8

```
ggaaagtaga tccgagaggg a                                              21
```

<210> SEQ ID NO 9
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2cn80

<400> SEQUENCE: 9
atttcagcgc tcacatgaca                                            20

<210> SEQ ID NO 10
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR2cn80

<400> SEQUENCE: 10
aggagctgga tggaaagtca                                            20

<210> SEQ ID NO 11
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2cn83

<400> SEQUENCE: 11
cttccgcaat cagaagaagc                                            20

<210> SEQ ID NO 12
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR2cn83

<400> SEQUENCE: 12
tgaatttgta gcgcacttcg                                            20

<210> SEQ ID NO 13
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2cn92

<400> SEQUENCE: 13
tgacatcagc tccagaatgc                                            20

<210> SEQ ID NO 14
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR2cn92

<400> SEQUENCE: 14
acccatattt cgccttctca                                            20

<210> SEQ ID NO 15
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn358

<400> SEQUENCE: 15
tgctttagcc ggagtgatct                                            20

```
<210> SEQ ID NO 16
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3cn358

<400> SEQUENCE: 16
cagcagcaaa tccaagtcaa                                                     20

<210> SEQ ID NO 17
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2sg15

<400> SEQUENCE: 17
caactgctag tcgtgggaca                                                     20

<210> SEQ ID NO 18
<211> LENGTH: 22
<212> TYPE: DNA
<213> ORGANISM: Artificial Sequence
<220> FEATURE:
<223> OTHER INFORMATION: Reverse primer sequence for marker ID:
      OBNJR2sg15

<400> SEQUENCE: 18
cgactcatga ccagtaaacc tg                                                  22

<210> SEQ ID NO 19
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2sg21

<400> SEQUENCE: 19
tttgctctgc tggagggtat                                                     20

<210> SEQ ID NO 20
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR2sg21

<400> SEQUENCE: 20
caacaggcat cgaagtagca                                                     20

<210> SEQ ID NO 21
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2sg31

<400> SEQUENCE: 21
cttgaattcg cgcagtatga                                                     20
```

<210> SEQ ID NO 22
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR2sg31

<400> SEQUENCE: 22
aaacagcgga ttcaccactc                                            20

<210> SEQ ID NO 23
<211> LENGTH: 20
<212> TYPE: DNA
<213> ORGANISM: Artificial Sequence
<220> FEATURE:
<223> OTHER INFORMATION: Forward primer sequence for marker ID:
      OBNJR2sg34

<400> SEQUENCE: 23
cccaggatta ttccctcatt                                            20

<210> SEQ ID NO 24
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR2sg34

<400> SEQUENCE: 24
gaacatggga gggatgaaga                                            20

<210> SEQ ID NO 25
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn80

<400> SEQUENCE: 25
tcgtcttcga acatgagacg                                            20

<210> SEQ ID NO 26
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3cn80

<400> SEQUENCE: 26
aaatgtcagc tttcatcgcc                                            20

<210> SEQ ID NO 27
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn201

<400> SEQUENCE: 27
gcagcagcat tcaggtacaa                                            20

-continued

<210> SEQ ID NO 28
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3cn201

<400> SEQUENCE: 28
gggagattat tcacgaggca                                              20

<210> SEQ ID NO 29
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn217

<400> SEQUENCE: 29
actccttatg ctgggaccct                                              20

<210> SEQ ID NO 30
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3cn217

<400> SEQUENCE: 30
tcgtgcagga atgtgaaatc                                              20

<210> SEQ ID NO 31
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn239

<400> SEQUENCE: 31
caaggcagca caacattcag                                              20

<210> SEQ ID NO 32
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3cn239

<400> SEQUENCE: 32
aatggcgtct acctttgtgg                                              20

<210> SEQ ID NO 33
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn328

<400> SEQUENCE: 33
cgtacagcag cagtagcagc                                              20

<210> SEQ ID NO 34

```
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3cn328

<400> SEQUENCE: 34
gctgcatttg tgaactgctc                                              20

<210> SEQ ID NO 35
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn356

<400> SEQUENCE: 35
tggagggaga aggtgagaaa                                              20

<210> SEQ ID NO 36
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3cn356

<400> SEQUENCE: 36
tccttgctgt gttcctttcc                                              20

<210> SEQ ID NO 37
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn391

<400> SEQUENCE: 37
cccacctcat cttctcatgg                                              20

<210> SEQ ID NO 38
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3cn391

<400> SEQUENCE: 38
cagcttgaag tagcccttgg                                              20

<210> SEQ ID NO 39
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3cn401

<400> SEQUENCE: 39
acctgtaaac cagcaccacc                                              20

<210> SEQ ID NO 40
<211> LENGTH: 20
```

-continued

```
<212> TYPE: DNA
<213> ORGANISM: Artificial Sequence
<220> FEATURE:
<223> OTHER INFORMATION: Reverse primer sequence for marker ID:
      OBNJR3cn401

<400> SEQUENCE: 40
tgacatggga ggaggaactc                                          20

<210> SEQ ID NO 41
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3sg98

<400> SEQUENCE: 41
accaaatcca agaccctccc                                          20

<210> SEQ ID NO 42
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3sg98

<400> SEQUENCE: 42
ttgtagaaga ggctcgtcgg                                          20

<210> SEQ ID NO 43
<211> LENGTH: 20
<212> TYPE: DNA
<213> ORGANISM: Artificial Sequence
<220> FEATURE:
<223> OTHER INFORMATION: Forward primer sequence for marker ID:
      OBNJR3sg137

<400> SEQUENCE: 43
ttgtgtggat tgcggttaaa                                          20

<210> SEQ ID NO 44
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR3sg137

<400> SEQUENCE: 44
cggaccttac ttcattcgga                                          20

<210> SEQ ID NO 45
<211> LENGTH: 20
<212> TYPE: DNA
<213> ORGANISM: Artificial Sequence
<220> FEATURE:
<223> OTHER INFORMATION: Forward primer sequence for marker ID:
      OBNJR4cn10

<400> SEQUENCE: 45
cacgacatat aagcgcgatg                                          20

<210> SEQ ID NO 46
<211> LENGTH: 20
<212> TYPE: DNA
```

```
<213> ORGANISM: Artificial Sequence
<220> FEATURE:
<223> OTHER INFORMATION: Reverse primer sequence for marker ID:
      OBNJR4cn10

<400> SEQUENCE: 46
tctgctggtg atgagctgtc                                                  20

<210> SEQ ID NO 47
<211> LENGTH: 20
<212> TYPE: DNA
<213> ORGANISM: Artificial Sequence
<220> FEATURE:
<223> OTHER INFORMATION: Forward primer sequence for marker ID:
      OBNJR4cn11

<400> SEQUENCE: 47
ctgtcatcgc cacaagctaa                                                  20

<210> SEQ ID NO 48
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR4cn11

<400> SEQUENCE: 48
ttgtggcgct tgagaagtta                                                  20

<210> SEQ ID NO 49
<211> LENGTH: 21
<212> TYPE: DNA
<213> ORGANISM: Artificial Sequence
<220> FEATURE:
<223> OTHER INFORMATION: Forward primer sequence for marker ID:
      OBNJR4cn14

<400> SEQUENCE: 49
cacaacatga acaaagaccc a                                                21

<210> SEQ ID NO 50
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR4cn14

<400> SEQUENCE: 50
agtggaatcc gaagcatttg                                                  20

<210> SEQ ID NO 51
<211> LENGTH: 20
<212> TYPE: DNA
<213> ORGANISM: Artificial Sequence
<220> FEATURE:
<223> OTHER INFORMATION: Forward primer sequence for marker ID:
      OBNJR4cn15

<400> SEQUENCE: 51
cagcatctcc gaactgtgaa                                                  20

<210> SEQ ID NO 52
<211> LENGTH: 20
<212> TYPE: DNA
<213> ORGANISM: Artificial Sequence
```

```
<220> FEATURE:
<223> OTHER INFORMATION: Reverse primer sequence for marker ID:
      OBNJR4cn15

<400> SEQUENCE: 52
aaacgatcat ctcctccacg                                               20

<210> SEQ ID NO 53
<211> LENGTH: 20
<212> TYPE: DNA
<213> ORGANISM: Artificial Sequence
<220> FEATURE:
<223> OTHER INFORMATION: Forward primer sequence for marker ID:
      OBNJR4cn16

<400> SEQUENCE: 53
ttcactctgc caggcctaat                                               20

<210> SEQ ID NO 54
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR4cn16

<400> SEQUENCE: 54
ctgtttgagc tgtgacggaa                                               20

<210> SEQ ID NO 55
<211> LENGTH: 23
<212> TYPE: DNA
<213> ORGANISM: Artificial Sequence
<220> FEATURE:
<223> OTHER INFORMATION: Forward primer sequence for marker ID:
      OBNJR4sg01

<400> SEQUENCE: 55
caaacttcaa cctcaacatt caa                                           23

<210> SEQ ID NO 56
<211> LENGTH: 20
<212> TYPE: DNA
<213> ORGANISM: Artificial Sequence
<220> FEATURE:
<223> OTHER INFORMATION: Reverse primer sequence for marker ID:
      OBNJR4sg01

<400> SEQUENCE: 56
gaggaggagg aggaagagga                                               20

<210> SEQ ID NO 57
<211> LENGTH: 21
<212> TYPE: DNA
<213> ORGANISM: Artificial Sequence
<220> FEATURE:
<223> OTHER INFORMATION: Forward primer sequence for marker ID:
      OBNJR4sg06

<400> SEQUENCE: 57
caaagagcca attagtttcc c                                             21

<210> SEQ ID NO 58
<211> LENGTH: 20
<212> TYPE: DNA
<213> ORGANISM: Artificial Sequence
<220> FEATURE:
```

```
<223> OTHER INFORMATION: Reverse primer sequence for marker ID:
      OBNJR4sg06

<400> SEQUENCE: 58
aggcgacgga ttcatagttg                                              20

<210> SEQ ID NO 59
<211> LENGTH: 18
<212> TYPE: DNA
<213> ORGANISM: Artificial Sequence
<220> FEATURE:
<223> OTHER INFORMATION: Sequence for attachment to a forward
      primer

<400> SEQUENCE: 59
tgtaaaacga cggccagt                                                18
```